US011259918B2

(12) United States Patent
Bressloff et al.

(10) Patent No.: US 11,259,918 B2
(45) Date of Patent: Mar. 1, 2022

(54) FRAME FOR AN IMPLANTABLE MEDICAL DEVICE AND A METHOD OF MANUFACTURING A FRAME FOR AN IMPLANTABLE MEDICAL DEVICE

(71) Applicant: CARENA HEALTHCARE LTD, Southampton (GB)

(72) Inventors: Neil W. Bressloff, Southampton (GB); Jonathan Bailey, Southampton (GB)

(73) Assignee: Carena Healthcare Ltd, Southampton (GB)

(*) Notice: Subject to any disclaimer, the term of this patent is extended or adjusted under 35 U.S.C. 154(b) by 255 days.

(21) Appl. No.: 16/339,217

(22) PCT Filed: Oct. 3, 2017

(86) PCT No.: PCT/GB2017/052961
§ 371 (c)(1),
(2) Date: Apr. 3, 2019

(87) PCT Pub. No.: WO2018/065763
PCT Pub. Date: Apr. 12, 2018

(65) Prior Publication Data
US 2019/0224008 A1    Jul. 25, 2019

(30) Foreign Application Priority Data

Oct. 3, 2016    (GB) ...................................... 1616777

(51) Int. Cl.
*A61F 2/24* (2006.01)
*A61F 2/852* (2013.01)

(52) U.S. Cl.
CPC .......... *A61F 2/2418* (2013.01); *A61F 2/2415* (2013.01); *A61F 2/852* (2013.01);
(Continued)

(58) Field of Classification Search
CPC ........ A61F 2/24; A61F 2/2412; A61F 2/2415; A61F 2/2418; A61F 2/852; A61F 2/89;
(Continued)

(56) References Cited

U.S. PATENT DOCUMENTS 6,730,118 B2 * 5/2004 Spenser ................ A61F 2/9524
623/1.24
7,935,144 B2    5/2011 Robin et al.
(Continued)

FOREIGN PATENT DOCUMENTS

CA    2825012 A1    7/2012
CA    2910434 A1    10/2015
(Continued)

OTHER PUBLICATIONS

"International Application Serial No. PCT/GB2017/052961, International Search Report dated Dec. 22, 2017", (Dec. 22, 2017), 4 pgs.
(Continued)

*Primary Examiner* — Robert A Lynch
(74) *Attorney, Agent, or Firm* — Schwegman Lundberg & Woessner, P.A.

(57) ABSTRACT

A frame for an implantable medical device, comprising: a first member, comprising a plurality of struts defining a plurality of cells, wherein the first member is annular and defines a longitudinal direction which is parallel to the axis of the first member, a radial direction, and a circumferential direction; a second member, comprising a plurality of struts and coupled to the first member at circumferentially distributed locations; wherein the second member overlaps a first end portion of the first member and extends beyond the first end portion of the first member.

15 Claims, 25 Drawing Sheets

(52) U.S. Cl.
CPC ........... *A61F 2210/0076* (2013.01); *A61F 2220/0058* (2013.01); *A61F 2220/0075* (2013.01); *A61F 2250/0007* (2013.01); *A61F 2250/0018* (2013.01); *A61F 2250/0039* (2013.01); *A61F 2250/0063* (2013.01)

(58) Field of Classification Search
CPC ........... A61F 2/90; A61F 2002/9155; A61F 2220/0058; A61F 2220/0075; A61F 2210/0076; A61F 2250/0007; A61F 2250/0018; A61F 2250/0039; A61F 2250/0063
See application file for complete search history.

(56) References Cited

U.S. PATENT DOCUMENTS

| | | | |
|---|---|---|---|
| 8,620,050 | B2 | 12/2013 | Liao et al. |
| 8,673,000 | B2 | 3/2014 | Tabor et al. |
| 9,125,741 | B2 | 9/2015 | Phung et al. |
| 2003/0139799 | A1 | 7/2003 | Ley et al. |
| 2008/0051866 | A1 | 2/2008 | Chen et al. |
| 2009/0210049 | A1 | 8/2009 | Thielen et al. |
| 2011/0245907 | A1 | 10/2011 | Pacetti |
| 2012/0163686 | A1 | 6/2012 | Liao et al. |
| 2013/0190726 | A1 | 7/2013 | Kesner et al. |
| 2013/0245751 | A1 | 9/2013 | Phung et al. |
| 2014/0121763 | A1 | 5/2014 | Duffy et al. |
| 2014/0142692 | A1 | 5/2014 | Ho |
| 2014/0163664 | A1 | 6/2014 | Goldsmith |
| 2014/0172083 | A1 | 6/2014 | Bruchman et al. |
| 2014/0187666 | A1 | 7/2014 | Aizenberg et al. |
| 2014/0277390 | A1 | 9/2014 | Ratz et al. |
| 2015/0119692 | A1 | 4/2015 | Mchenry et al. |
| 2015/0135506 | A1 | 5/2015 | White |
| 2015/0178938 | A1 | 6/2015 | Gorman, III et al. |
| 2015/0201500 | A1* | 7/2015 | Shinar ............... B29C 64/135 425/132 |
| 2015/0202348 | A1 | 7/2015 | Dvir et al. |
| 2015/0209022 | A1 | 7/2015 | Ruppert et al. |
| 2015/0216552 | A1 | 8/2015 | Hefer |
| 2015/0282929 | A1 | 10/2015 | Rodriguez |
| 2015/0282931 | A1 | 10/2015 | Brunnett et al. |
| 2015/0306282 | A1 | 10/2015 | Scanlon et al. |
| 2015/0342763 | A1 | 12/2015 | Hsiao |
| 2015/0359633 | A1 | 12/2015 | Dingmann et al. |
| 2015/0359634 | A1 | 12/2015 | Dingmann et al. |
| 2016/0009029 | A1 | 1/2016 | Cohen et al. |
| 2016/0080741 | A1 | 1/2016 | Glossop |
| 2016/0051362 | A1 | 2/2016 | Cooper et al. |
| 2016/0128830 | A1 | 5/2016 | Phung et al. |
| 2018/0055665 | A1* | 3/2018 | Gorochow ............... A61F 2/885 |

FOREIGN PATENT DOCUMENTS

| | | |
|---|---|---|
| DE | 102011108143 A1 | 1/2013 |
| WO | WO-2011137336 A1 | 11/2011 |
| WO | WO-2012100100 A2 | 7/2012 |
| WO | WO-2012100100 A3 | 10/2012 |
| WO | WO-2014164302 A1 | 10/2014 |
| WO | WO-2015013536 A2 | 1/2015 |
| WO | WO-2015013536 A3 | 4/2015 |
| WO | WO-2015051380 A2 | 4/2015 |
| WO | WO-2015070249 A1 | 5/2015 |
| WO | WO-2015112923 A1 | 7/2015 |
| WO | WO-2015114463 A2 | 8/2015 |
| WO | WO-2015121674 A1 | 8/2015 |
| WO | WO-2015134853 A1 | 9/2015 |
| WO | WO-2015138032 A2 | 9/2015 |
| WO | WO-2015149043 A1 | 10/2015 |
| WO | WO-2015153986 A1 | 10/2015 |
| WO | WO-2015171743 A2 | 11/2015 |
| WO | WO-2015179423 A1 | 11/2015 |
| WO | WO-2015194961 A1 | 12/2015 |
| WO | WO-2015195838 A1 | 12/2015 |
| WO | WO-2015200707 A1 | 12/2015 |
| WO | WO-2015200723 A1 | 12/2015 |
| WO | WO-2016007717 A1 | 1/2016 |
| WO | WO-2016029166 A1 | 2/2016 |
| WO | WO-2016044651 A1 | 3/2016 |
| WO | WO-2016090093 A1 | 6/2016 |
| WO | WO-2016092423 A1 | 6/2016 |
| WO | WO-2016116748 A1 | 7/2016 |

OTHER PUBLICATIONS

"International Application Serial No. PCT/GB2017/052961, Written Opinion dated Dec. 22, 2017", (Dec. 22, 2017), 6 pgs.

Bailey, Jonathon, et al., "Assessing the impact of including leaflets in the simulation of TAVI deployment into a patient-specific aortic root", Computer methods in biomechanics and biomedical engineering 19.7, (2016), pp. 733-744.

Bailey, Jonathon, "Implications for leaflet behaviour in heavily calcified patient-specific aortic roots: simulation of transcatheter aortic valve implantation", Diss. University of Southampton, (2015), 232 pgs.

Bailey, Jonathon, et al., "The impact of imperfect frame deployment and rotational orientation on stress within the prosthetic leaflets during transcatheter aortic valve implantation", Journal of biomechanics 53, (2017), pp. 22-28.

Collas, Valérie, et al., "Transcatheter aortic valve implantation: review and current state of the art", EMJ Int Cardiol 1, (2014), pp. 52-61.

Legg, Murray, et al., "The design and development of a stented tissue mitral and aortic heart valve replacement for human implantation: cardiovascular topics", Cardiovascular Journal of Africa 23.3, (2012), pp. 126-130.

Likosky, Donald S., et al., "Long-term survival of the very elderly undergoing aortic valve surgery", Circulation 120.11_suppl1, (2009), pp. S127-S133.

Ludman, Peter F., et al., "Transcatheter aortic valve implantation in the United Kingdom: temporal trends, predictors of outcome, and 6-year follow-up: a report from the UK Transcatheter AorticValve Implantation (TAVI) Registry, 2007 to 2012", Circulation 131.13, (2015), pp. 1181-1190.

Nkomo, Vuyisile T., et al., "Burden of valvular heart diseases: a population-based study", The Lancet 368.9540, (2006), pp. 1005-1011.

Osnabrugge, Ruben LJ, et al., "Aortic stenosis in the elderly: disease prevalence and number of candidates for transcatheter aortic valve replacement: a meta-analysis and modeling study", Journal of the American College of Cardiology 62.11, (2013), pp. 1002-1012.

Reynolds, Matthew R., et al., "Cost-effectiveness of transcatheter aortic valve replacement compared with surgical aortic valve replacement in high-risk patients with severe aortic stenosis: results of the PARTNER (Placement of Aortic Transcatheter Valves) trial (Cohort A", Journal of the American College of Cardiology 60.25, (2012), pp. 2683-2692.

Schymik, Gerhard, et al., "Howto adapt the implantation technique for the new SAPIEN 3 transcatheter heart valve design". Journal of interventional cardiology 28.1, (2015), pp. 82-89.

* cited by examiner

Support structures

Crimped Shape

FRAME FOR AN IMPLANTABLE MEDICAL DEVICE AND A METHOD OF MANUFACTURING A FRAME FOR AN IMPLANTABLE MEDICAL DEVICE

PRIORITY APPLICATIONS

This application is a U.S. National Stage Filing under 35 U.S.C. 371 from International Application No. PCT/GB2017/052961, filed on Oct. 3, 2017, and published as WO2018/065763 on Apr. 12, 2018, which claims the benefit of priority to United Kingdom Application No. 1616777.7, filed on Oct. 3, 2016; the benefit of priority of each of which is hereby claimed herein, and which applications and publication are hereby incorporated herein by reference in their entirety.

FIELD

The present invention relations to frames for implantable medical devices and methods of manufacturing such frames.

BACKGROUND

Implantable medical devices include devices such as stents and valves. These devices are implanted into a patient and it is usually intended that they remain implanted in the patient permanently. Such implantable medical devices may comprise a frame which provides the structure of the device.

Transcatheter implantation methods have been developed, particularly for the aortic valve. A conventional implantable device for a heart valve comprises a metal frame, a skirt, which may be stitched to the frame, and a set of three leaflets, which may be stitched to the skirt and secured to the commissures of the frame. The metal frame comprises a plurality of struts defining a plurality of cells and may be cylindrical. This type of device may be crimped on a balloon catheter so that it can moved into position percutaneously before being opened through inflation of the balloon.

The SAPIEN 3 device manufactured by Edwards Lifesciences is an example of such a device. The device has a radially contracted configuration when it is moved into position and a radially expanded configuration when deployed. The total length of the device in the radially expanded state is less than the total length of the device in the radially contracted state. This is referred to as foreshortening, and can make valve positioning more difficult and increase the chance of dislodging calcified plaques in the native valve. Foreshortening may be larger than a third of the overall device height and may increase proportionally with valve size.

U.S. Pat. No. 8,673,000 describes some further examples of implantable devices for a heart valve. In this document, devices having wings which extend outwardly from the frame and are used to dock the device against the top aspect of the native leaflets when the device is implanted are disclosed. The device also exhibits foreshortening.

BRIEF DESCRIPTION OF FIGURES

Systems and methods in accordance with non-limiting embodiments will now be described with reference to the accompanying figures in which.

STATEMENTS OF INVENTION

Figure 1A:
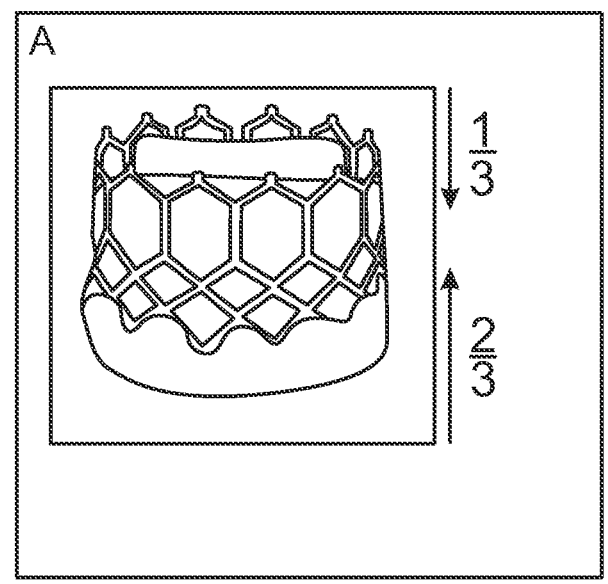
FIG. 1(a) shows a prior art Transcatheter Aortic Valve Implantation device, the SAPIEN 3 device manufactured by Edwards Lifesciences in its radially expanded state (A) and crimped state (B)
Figure 1A:
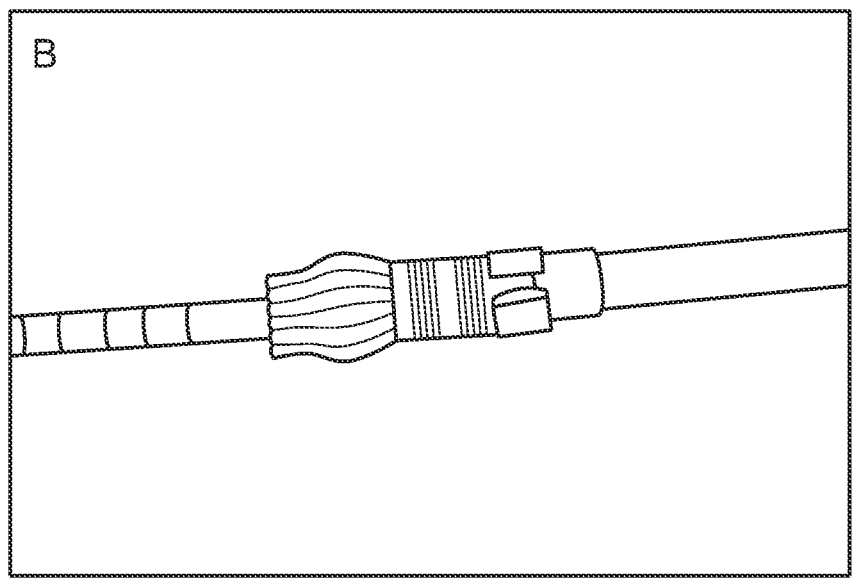

According to a first aspect of the present invention there is provided a frame for an implantable medical device, comprising:
   a first member, comprising a plurality of struts defining a plurality of cells, wherein the first member is annular and defines a longitudinal direction which is parallel to the axis of the first member, a radial direction, and a circumferential direction;
   a second member, comprising a plurality of struts and coupled to the first member at circumferentially distributed locations;
   wherein the second member overlaps a first end portion of the first member and extends beyond the first end portion of the first member.

In an embodiment, the first member defines more cells than the second member.

In an embodiment, the first member comprises more circumferential rings of struts which are connected to each other through struts extending in a direction which has a component in the circumferential direction than the second member.

In an embodiment, the device is an implantable heart valve device. In an embodiment, the device is a stent. The device may be an aortic stent.

In an embodiment, a first end portion of the second member is separate from the first end portion of the first member. By separate, it is meant that the first end portion of the first member is not directly connected to the second member, i.e. it is connected to the second member only through a coupling at a different location on the first member.

The second member extends beyond the first end portion of the first member in the longitudinal direction.

The first member and second member form two layers. The frame may comprise more than two layers.

In an embodiment the first member is integral. The first member may be integral with the second member.

In an embodiment, the second member is annular and is radially displaced from the first member such that one of the first member and the second member is arranged around the other. The first member and second member may be concentrically arranged.

The frame is configured to be radially contracted and expanded, between a radially contracted state and a radially expanded state, wherein a change in length of the first member between the radially contracted state and the radially expanded state is independent of a change in length of the second member between the radially contracted state and the radially expanded state.

In an embodiment, the part of the first member between the first end portion and the location at which it is coupled to the second member comprises a plurality of vertices between the struts.

In an embodiment, the second member comprises one or more rings of cells, each of which are connected to other rings of cells only through struts which do not have a component in the circumferential direction. The second member may be located at a middle portion of the frame.

In a further embodiment, the first member comprises one or more rings of cells, each of which are connected to other rings of cells only through struts which do not have a component in the circumferential direction.

In an embodiment, the change in length of the first member between the radially contracted state and the radially expanded state is more than the change in length of the second member between the radially contracted state and the radially expanded state.

In an embodiment, the first member comprises more vertices connected between three or more struts extending in a direction which has a component in the circumferential direction than the second member.

In an embodiment, the second member comprises a plurality of first struts having a first end and a second end, and wherein the direction from the first end to the second end has a component in the longitudinal direction and is orthogonal to the circumferential direction. In a further embodiment, the first member and the second member are coupled at the first struts. Each first strut may overlap at least one cell defined by the first member. The first ends of the first struts extend beyond the first member. The first struts may extend from the location at which the first member is coupled to the second member to the first end of the second member.

In an embodiment, the second member comprises one or more circumferential rings of struts including an outer ring of struts which is closest to the first end of the second member. The first member comprises one or more circumferential rings of struts including an outer ring of struts which is closest to the first end of the first member. The outer ring of struts in the second member is connected to the part of the second member which is connected to the first member through less struts which have a component in the circumferential direction than the outer ring of struts in the first member is connected to the part of the first member which is connected to the second member.

In an embodiment, any other rings of struts in the second member are connected to the outer ring only through struts which do not have a component in the circumferential direction.

In an embodiment, the frame further comprises a third member comprising a plurality of struts having a first end and a second end, and wherein the direction from the first end to the second end has a component in the longitudinal direction and is orthogonal to the circumferential direction, wherein each strut is coupled to a first strut in the second member which is aligned in the longitudinal direction with the strut.

In an embodiment, the radial distance between the first member and the second member at the first end portion of the first member is greater than 40 microns.

In an embodiment, the device comprises a plurality of coupling portions, extending in a direction which has a component in the radial direction, coupling the first member and the second member. Each coupling portion may branch from a strut of the first member or the second member.

In an embodiment, the first member defines more rings of cells than the second member.

In an embodiment, the second member comprises a plurality of struts defining a plurality of cells.

The device may be suitable for transcatheter aortic valve implantation (TAVI). The device may be a balloon expandable device or a self-expanding device. Alternatively, the device may be suitable for surgical implantation.

In an embodiment, the second member is coupled to the first member inside the first member, and the portion of the second member which extends beyond the first end portion of the first member flares radially outwards.

In an embodiment, the frame further comprises a third member, comprising a plurality of struts and coupled to the first member at circumferentially distributed locations, wherein the third member overlaps a second end portion of the first member and extends beyond the second end portion of the first member.

In an embodiment, a second end portion of the third member is separate from the second end portion of the first member. The third member may be annular and radially displaced from the first member such that one of the first member and the third member is arranged around the other. In an embodiment, the radial distance between the first member and the third member at the second end portion of the first member is greater than 40 microns.

In an embodiment, the second member is coupled to the first member at a first longitudinal location, and the third member is coupled to the first member at a second, different longitudinal location. In an embodiment, the third member is coupled to the first member at the first end of the first member, and the second member is coupled to the first member at the second end of the first member.

In an embodiment, the second member and the third member are displaced relative to each other in the longitudinal direction between the radially contracted state and the radially expanded state. The second member and the third member move in opposite longitudinal directions. The second member and third member are coupled to the first member at locations on the first member which move relative to each other in the longitudinal direction between the radially contracted state and the radially expanded state. The second member extends beyond the first end of the first member, but is coupled at a longitudinal location on the first member which moves in the direction from the first end towards the second end of the first member when the frame transitions to the radially contracted state. The third member extends beyond the second end of the first member, but is coupled at a longitudinal location on the first member which moves in the direction from the second end towards the first end of the first member when the frame transitions to the radially contracted state.

In an embodiment, the total frame length is the same in the radially contracted state and the radially expanded state. In an embodiment, the total frame length in the radially contracted state and the total frame length in the radially expanded state are within 20% of the total frame length in the radially contracted state of each other. In an embodiment, the total frame length in the radially contracted state and the total frame length in the radially expanded state are within 10% of the total frame length in the radially contracted state of each other. In an embodiment, the total frame length in the radially contracted state and the total frame length in the radially expanded state are within 5% of the total frame length in the radially contracted state of each other.

In an embodiment, a change in length of the second member is equal to the longitudinal displacement of the second member, and a change in length of the third member is equal to the longitudinal displacement of the third member.

In an embodiment, the total extension of the frame at the first end between the radially expanded state and the radially contracted state is equal to the difference between the change in length of the second member 202 and the displacement of the second member 202 towards the second end of the frame B. Similarly, the total extension of the frame at the second end is equal to the difference between the change in length of the third member 203 and the displacement of the third member 203 towards the first end of the frame A. The overall change in length of the whole frame is given by the sum of the total extension at the first end and at the second end.

In an embodiment, the change of length of the first member, the second member and the third member are independent of each other. The longitudinal displacement of the second member depends on the change of length of the first member and the longitudinal displacement of the third member depends on the change of length of the first member.

In an embodiment, the frame is formed by additive manufacturing.

According to a second aspect of the present invention, there is provided implantable heart valve device, comprising the frame and further comprising:
a skirt coupled to the frame; and
a plurality of leaflets.

According to a third aspect of the present invention there is provided method of manufacturing a frame for an implantable medical device, comprising:
forming a plurality of struts defining a plurality of cells by additive manufacturing.

In an embodiment, the method further comprises:
forming a plurality of support structures;
wherein forming the struts comprises:
forming a ring comprising a plurality of struts on support structures, wherein the struts extend away from the support structures;
wherein the method further comprises removing the support structures from the struts.

In an embodiment, forming the struts comprises:
forming a first member, comprising a plurality of struts defining a plurality of cells, wherein the first member is annular and defines a longitudinal direction which is parallel to the axis of the first member, a radial direction, and a circumferential direction;
forming a second member, comprising a plurality of struts, coupled to the first member at circumferentially distributed locations;
wherein the second member overlaps a first end portion of the first member and extends beyond the first end portion of the first member, and wherein a first end portion of the second member is separate from the first end portion of the first member;
wherein the first member and the second member are integrally formed.

In an embodiment, the method further comprises:
forming a plurality of support structures;
wherein forming the first member comprises forming a first ring comprising a plurality of struts on support structures, wherein the struts extend away from the support structures,
wherein the method further comprises removing the support structures from the struts.

In an embodiment, the method further comprises:
forming a plurality of further support structures coupling the first member and the second member at the first end portion of the first member.

Removing the support structures may comprise electropolishing.

According to a fourth aspect of the present invention there is provided a frame for an implantable medical device, formed by forming a plurality of struts defining a plurality of cells by additive manufacturing. The struts may be formed by metal sintering.

According to a fifth aspect of the present invention there is provided method of manufacturing a frame for an implantable medical device, comprising:
forming a first member, comprising a plurality of struts defining a plurality of cells, wherein the first member is annular and defines a longitudinal direction which is parallel to the axis of the first member, a radial direction, and a circumferential direction;
forming a second member, comprising a plurality of struts and coupled to the first member at circumferentially distributed locations;
wherein the second member overlaps a first end portion of the first member and extends beyond the first end portion of the first member, and wherein a first end portion of the second member is separate from the first end portion of the first member.

The first member may be welded, sutured, mechanically coupled or bonded to the second member.

DETAILED DESCRIPTION

Surgical methods have been used to replace diseased or defective heart valves. Surgical methods involve open heart surgery, removal of the native valve and the suturing of a prosthetic device in the valve opening. In recent years, transcatheter implantation methods have been developed, particularly for the aortic valve. FIG. 1(a) shows a prior art Transcatheter Aortic Valve Implantation (TAVI) device, the SAPIEN 3 device manufactured by Edwards Lifesciences in its radially expanded state (A) and crimped state (B). The device comprises a cylindrical metal frame, a skirt stitched to the frame (the white material on the inside of the frame that is folded around the lower edge onto the outside of the frame) and a set of three leaflets that are stitched to the skirt and secured to the commissures of the frame. There are three commissures, defined as the region where the leaflet ends are joined to each other and the frame. Leaflets may be manufactured from bovine or porcine pericardium for example.

This type of device is crimped on a balloon catheter, also shown in part B of the figure, so that it can moved into position percutaneously before being opened, or deployed, through inflation of the balloon.

Alternative devices are self-expanding devices, for example made of materials such as Nitinol, which have shape memory. For these devices, instead of inflating a balloon to open, self-expansion occurs when a sheath is slid away along the catheter. An example of such a self-expanding TAVI device is the CoreValve device manufactured by Medtronic.

Other implantable devices such as stents may be implanted in the body in a similar manner.

Figure 1B:
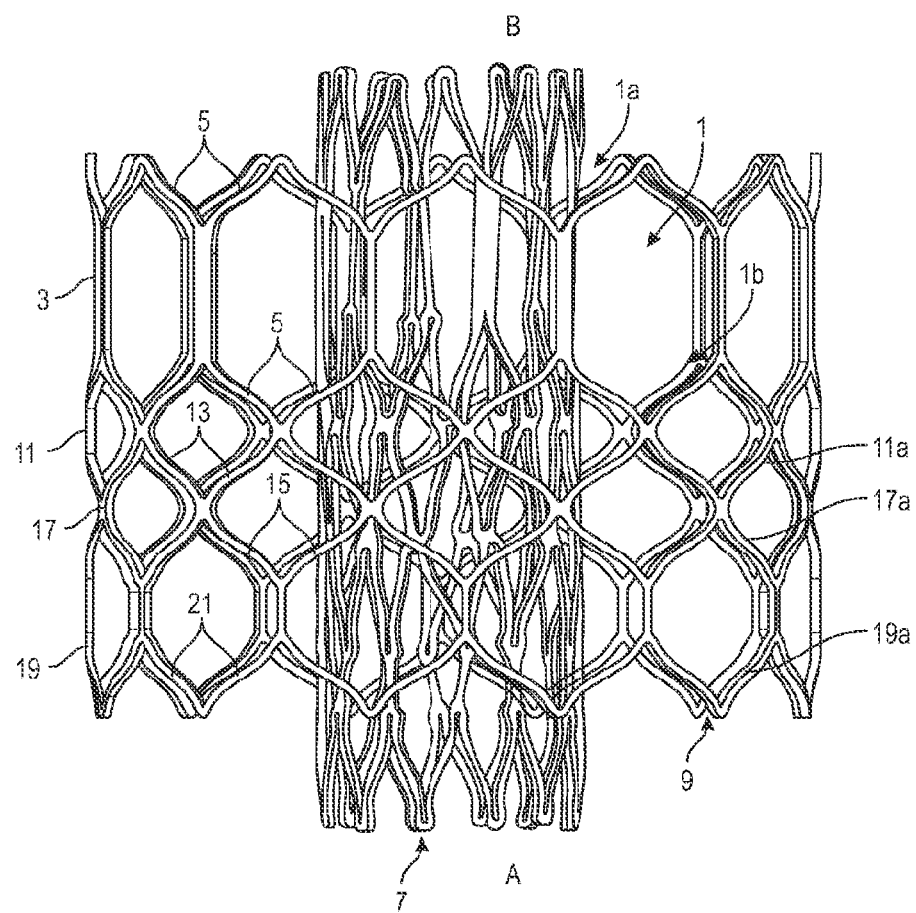
FIG. 1(b) is a schematic illustration of a modelled frame for an implantable heart valve device in which there are no overlapping members.
Figure 1C:
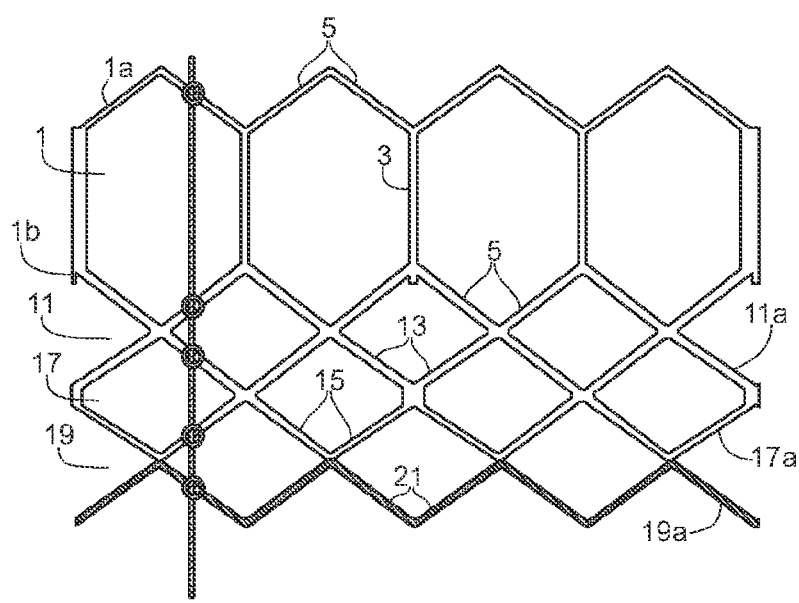
FIG. 1(c) shows the frame in an unwrapped illustration.

FIG. 1(b) is a schematic illustration of a modelled frame for an implantable medical device in which there are no overlapping members. The frame may be for an implantable heart valve device for example. The frame comprises a plurality of struts defining a plurality of cells. The cells are the spaces enclosed by the struts. The frame comprises vertices connected between the struts. The vertices are the connection portions between two or more struts. The vertices are hinged portions of the frame. They form the corners, i.e. vertices of the cells. FIG. 1(c) shows the frame in an unwrapped configuration.

The frame comprises a first ring of larger cells 1 at one end of the device. This first ring 1 comprises a plurality of struts 3 extending in the longitudinal direction. At each end of each strut 3, two further struts 5 are connected through a vertex. Each further strut 5 is connected at the other end to the adjacent further strut 5, forming two circumferential rings 1a and 1b of struts 5, one at each end of the longitudinal struts 3. The cells in the ring 1 are formed between the longitudinal struts 3 and the further struts 5. The further struts 5 extend in a direction which has a component in the circumferential direction. As the frame moves from the radially contracted state 7 to the radially expanded state 9 the orientation of the further struts 5 changes, causing the longitudinal struts 3 to move apart.

The frame comprises a further ring of cells 11, formed by struts 13, each connected at one end to the vertices between the further struts 5 and at the other end to the adjacent strut 13. Struts 13 form a further ring 11a of struts. Every other vertex in the ring 1b has four struts connected, two struts 5 in the ring 1b and two struts 13 from the ring 11a, each extending in a direction which has a component in the circumferential direction. The ring 1b and the ring 11a are thus connected through vertices connected to four struts, each extending in a direction which has a component in the circumferential direction.

A further ring of cells 17 is formed by struts 15, each connected at one end to the vertices between the struts 13 and at the other end to the adjacent strut 15. Struts 15 form a further ring of struts 17a. Every other vertex in the ring 11a has four struts connected, two struts 13 in the ring 11a and two struts 15 from the ring 17a, each extending in a direction which has a component in the circumferential direction. The ring 11a and the ring 17a are thus connected through vertices connected to four struts, each extending in a direction which has a component in the circumferential direction.

A further ring of cells 19 is formed by struts 21, each connected at one end to the vertices between the struts 15 and at the other end to the adjacent strut 21. Struts 21 form a further ring of struts 19a. Every other vertex in the ring 17a has four struts connected, two struts 15 in the ring 17a and two struts 21 from the ring 19a, each extending in a direction which has a component in the circumferential direction. The ring 17a and the ring 19a are thus connected through vertices connected to four struts, each extending in a direction which has a component in the circumferential direction.

There are four rings of struts, 1b, 11a, 17a, 19a, each comprising struts extending in a direction having a component in the circumferential directions. These rings of struts 1b, 11a, 17a 19a are connected through vertices, connected to two struts from one ring and two struts from the adjacent ring, each strut extending in a direction having a component in the circumferential direction.

The radial stiffness of the frame is proportional to the number of circumferential rings of struts. In this frame there are five rings, 1a, 1b, 11a, 17a, 19a. A line drawn through the frame in the longitudinal direction will cross a maximum of five struts, as shown in FIG. 1(c) for example.

When the frame moves from the radially contracted state 7 to the radially expanded state 9, each of the struts extending in a direction having a component in the circumferential direction changes orientation. These struts have a smaller component in the circumferential direction in the radially contracted state than in the radially expanded state. These struts have a larger component in the longitudinal direction in the radially contracted state than in the radially expanded state. This results in the length of the device in the radially expanded state being less than the length of the device in the radially contracted state. This is referred to as foreshortening.

The longitudinal struts 3 do not change orientation, and thus do not contribute to the change in length of the frame.

There are two outer rings of struts, 1a and 19a, each comprising struts extending in a direction having a component in the circumferential direction. These struts extend to the end of the frame, and thus the change in orientation of these struts contributes to the change in length of the frame.

The ring 1a is at the second end of the frame B and connected to the longitudinal struts 3. The change in length in the longitudinal direction of this ring 1a changes the distance of the second end of the frame B from the longitudinal struts 3.

The rings of struts 1b, 11a, 17a 19a are connected through vertices, connected to two struts from one ring and two struts from the adjacent ring, each strut extending in a direction having a component in the circumferential directions. The change in length in the longitudinal direction of these four rings 1b, 11a, 17a, 19a changes the distance of the first end of the frame A from the longitudinal struts 3.

Thus as the frame moves from the radially expanded state 9 to the radially contracted state 7, the length increases at the second end of the frame B by the change in length of the first ring 1a, and the length increases at the first end of the frame A by the change in length of the four rings 1b, 11a, 17a, 19a.

The total amount of foreshortening for the frame is equal to the sum of the foreshortening of each ring of struts. In this case, since all the struts having a component in the circumferential direction are the same, the total foreshortening is equal to the foreshortening of a single strut multiplied by five.

As described above, when the frame is crimped, its axial length, i.e. its length along the longitudinal direction increases. Since the length of the frame in the radially expanded configuration is the relevant length, in practice this length is fixed, and the foreshortening effect results in a longer length of the frame in the radially contracted configuration.

Longer length in the radially contracted configuration can cause problems during insertion of the device, when it needs to work its way around the complicated arteries.

Furthermore, during deployment, specific parts of the native aortic root are lined up with either the upper most, or lower most edges of the prosthetic valve, whilst still in the radially contracted configuration. If the device foreshortens to a large degree, this means that the clinician will need to gauge the expected foreshortening as well as the alignment, so that the frame is correctly aligned once expanded. The effect of foreshortening may limit the clinician to having to line up a specific edge. For example, in the modelled frame, the second end of the frame changes length less than the first end of the frame (relative to the fixed longitudinal struts 3) and thus the clinician may be required to align the upper edge of the frame.

Frames based on the design shown in FIG. 1 may be manufactured using a laser to cut away unwanted material from a tube for example. The laser-cut, closed-cell configuration of the frame in FIG. 1 causes unwanted foreshortening during deployment, which makes valve positioning more difficult and which can increase the chance of dislodging calcified plaques in the native valve. In some cases, the amount of foreshortening may be larger than a third of the overall device height, and may increase proportionally with valve size.

Figure 2A:
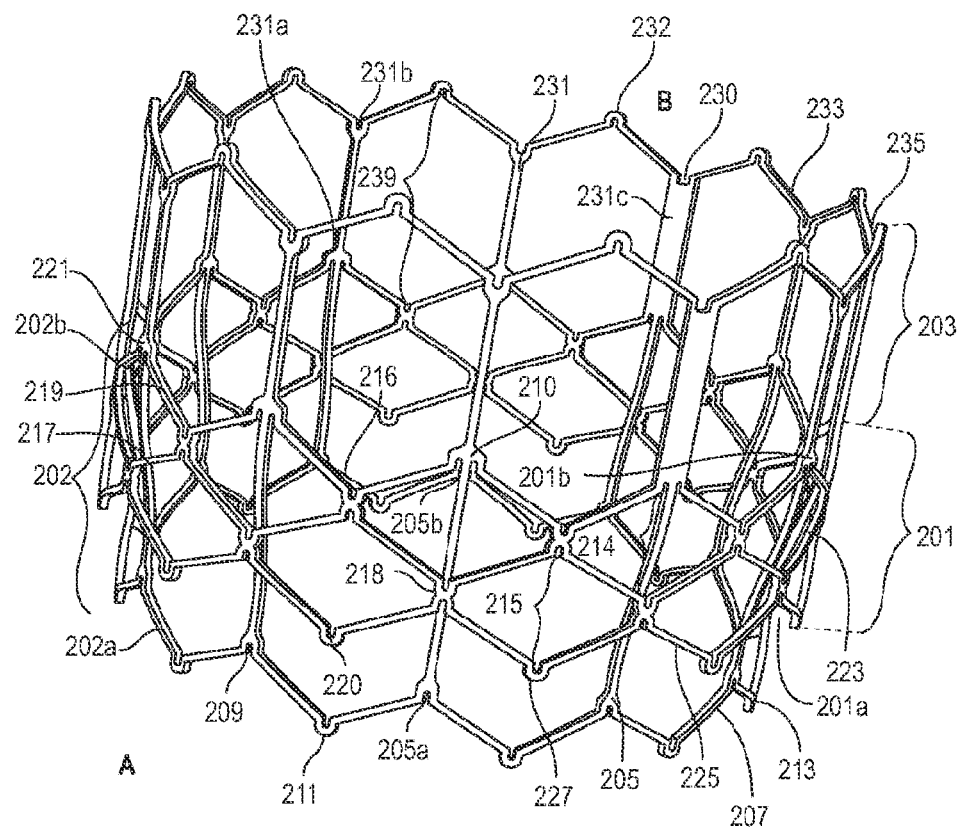
FIG. 2(a) is a schematic illustration of a frame for an implantable medical device in accordance with a first embodiment of the present invention.
Figure 2B:
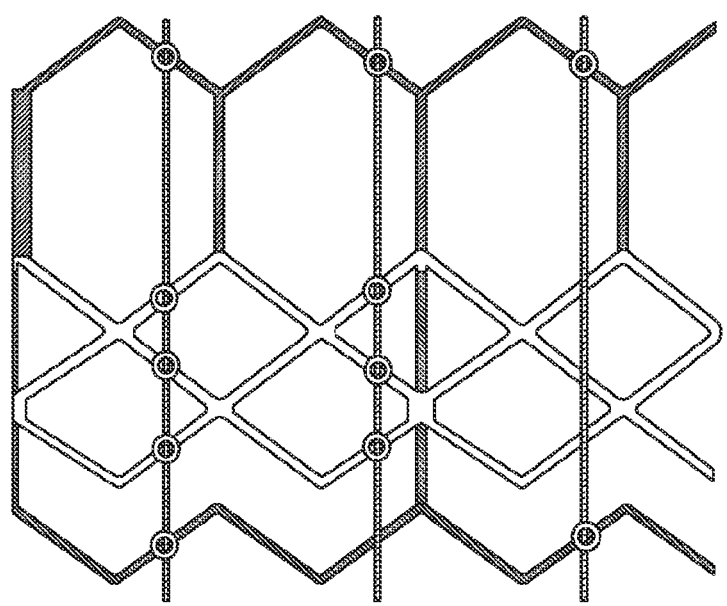
FIG. 2(b) shows the frame in an unwrapped illustration.
Figure 2C:
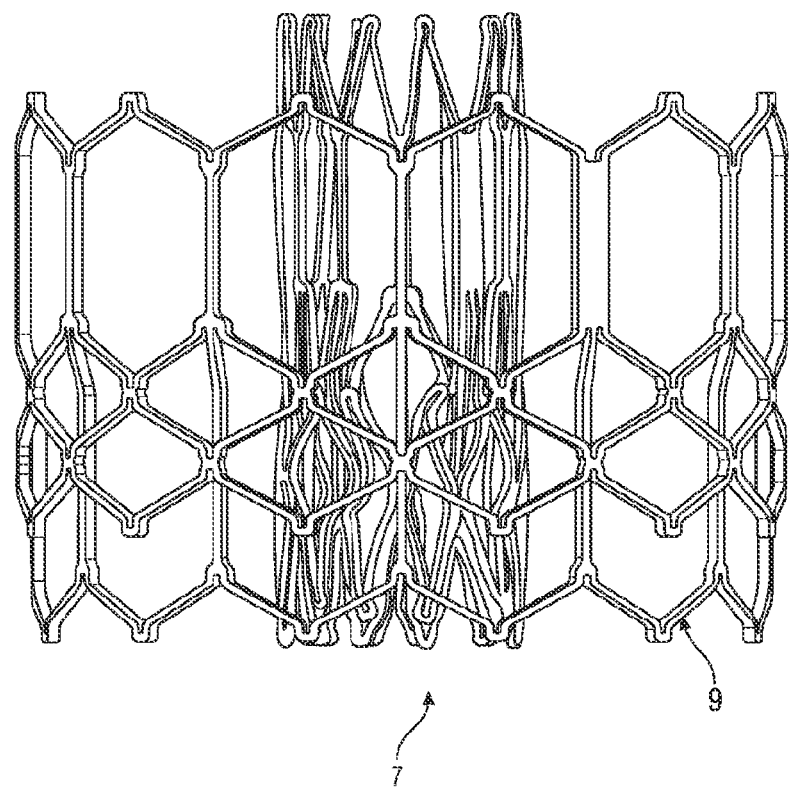
FIG. 2(c) shows the frame in a radially expanded state and a radially contracted state.
Figure 2C:
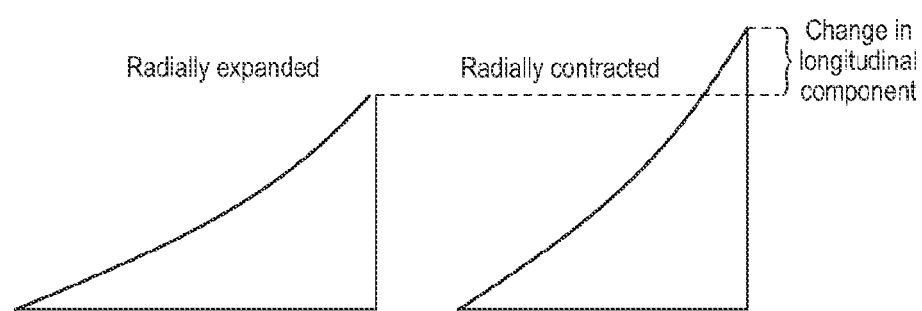

FIG. 2(a) is a schematic illustration of a frame for an implantable medical device in accordance with a first embodiment of the present invention. The frame may be for an implantable heart valve device for example. FIG. 2(b) shows the frame in an unwrapped illustration. The unwrapped illustration corresponds to the frame if it was cut along one side in the longitudinal direction, such that it is unrolled to form a rectangle. FIG. 2(c) shows the frame in a radially expanded state and a radially contracted state.

The frame comprises a first end A and a second end B. In an embodiment, the frame is a cylindrical shape.

The frame is a multi-layered frame. The frame comprises a first member 201, which corresponds to a first layer, comprising a plurality of struts defining a plurality of cells and a second member 202, which corresponds to a second layer, comprising a plurality of struts. The cells are the spaces enclosed by the struts.

In an embodiment, the first member defines more cells than the second member. In this embodiment, the second member 202 does not define any cells. In this embodiment, the first member defines 24 cells.

The first member 201 is annular and defines a longitudinal direction which is parallel to the axis of the first member, a radial direction, and a circumferential direction. The first member 201 and the second member 202 are coupled at circumferentially distributed locations.

The first member 201 comprises a first end portion 201a and a second end portion 201b. The first end portion 201a is closer to the first end of the frame A and the second end portion 201b is closer to the second end of the frame B. The second member 202 comprises a first end portion 202a and a second end portion 202b. The first end portion 202a is closer to the first end of the frame A and the second end portion 202b is closer to the second end of the frame B.

The second member 202 overlaps the first end portion 201a of the first member 201 and extends beyond the first end portion 201a of the first member 201. The second member 202 overlaps the first end portion 201a of the first member 201 in the radial direction. The first end portion 202a of the second member 202 is separate from the first end portion 201a of the first member 201.

As for the frame described in relation to FIG. 1, when the frame is crimped, its axial length increases. The multiple layers allow the frame to have reduced amount of length change between the radially contracted state and the radially expanded state, whilst maintaining radial stiffness, since the layers change length independently of each other. Reducing the extent of the foreshortening means that the length of the frame during deployment is reduced, meaning that it more easily works its way around the complicated arteries. Furthermore, alignment of the device with the native tissue is easier, since the device foreshortens less.

In an embodiment, the first member 201 and the second member 202 each have discrete rotational symmetry. In an embodiment, the first member 201 and the second member 202 have discrete rotational symmetry of the 3rd order. Alternatively, the frame has no rotational symmetry.

The second member 202 is longer than the first member 201. The second member 202 is coupled to the first member 201 at the second end portion 202b of the second member 202. However, the second member 202 may be coupled to the first member 201 at any point along the second member 202, other than the first end portion 202b of the second member 202 which is separate from the first member 201.

The first member 201 is coupled to the second member 202 at a second end portion 201b of the first member 201.

The second member 202 comprises a plurality of first struts 205 having a first end portion 205a and a second end portion 205b. The first end portion 205a is closer to the first end of the frame A and the second end portion 205b is closer to the second end of the frame B. The direction from the first end 205a to the second end 205b has a component in the longitudinal direction and is orthogonal to the circumferential direction. In this case the direction from the first end 205a to the second end 205b has a component in the longitudinal direction and in the radial direction, such that the part of the second member 202 which overlaps the first end portion 201a of the first member 201 is radially spaced from the first end portion 201a of the first member.

In an embodiment, the radial distance between the first member and the second member at the first end portion of the first member is greater than 40 microns. In an embodiment, the radial distance between the first member and the second member at the first end portion of the first member is greater than 80 microns. In an embodiment, it is greater than 100 microns. In an embodiment, it is between 40 microns and 200 microns.

Each first strut 205 overlaps at least one cell defined by the first member 201. In this frame, each first strut 205 overlaps one cell defined by the first member 201.

The second member 202 is coupled to the first member 201 at the second end portions 205b of the first struts 205, which are located at the second end portion 202b of the second member 202. The first end portions 205a of the first struts 205 are separate from the first member 201. The second member 202 is only coupled to the first member 201 at the second end portions 205b of the first struts 205. The first end portion 205a of the first struts 205 extend beyond the first member 201 in the longitudinal direction.

The second member 202 is annular. The second member 202 is radially displaced from the first member, such that the first member 201 is arranged around the second member 202. Alternatively however, the second member 202 is arranged around the first member 201. In an embodiment, the first member 201 and the second member 202 are concentrically arranged.

The frame comprises vertices connected between the struts. The vertices are the connection portions between two or more struts. The vertices are hinged portions of the frame. They form the corners, i.e. vertices, of the cells.

The second member 202 comprises a plurality of second struts 207 extending in a direction having a component in the circumferential direction. In this case, the second struts extend in a direction having a component in the longitudinal direction and a component in the circumferential direction. They may extend in a direction also having a component in the radial direction for example.

The second struts are connected at one end to the first struts through first vertices 209. Two second struts 207 are connected to each first strut 205 through a first vertex 209. In an embodiment, the second struts are connected to the first end portion 205a of the first struts 205 at the first end of the frame A, but they may be connected at a different location. Each second strut 207 is connected at the other end to the adjacent second strut 207 connected to the adjacent first strut 205 through a second vertex 211. The second struts 207 form a first ring of struts 213. Each pair of second struts 207 forms a V shape in the longitudinal direction. The second struts 207 thus form a zig-zag configuration around the first ring 213, such that every other vertex is displaced from the intervening vertices in the longitudinal direction. The second vertices 211 are displaced closer to the first end A than the first vertices 209.

In this embodiment, the second member 202 comprises the first struts 205 and the second struts 207, which form a trough shape, i.e. do not define a complete cell. However, in an embodiment, the second member 202 may comprise further struts such that the second member 202 also comprises a plurality of struts defining a plurality of cells.

The frame is configured to be radially contracted and expanded, between a radially contracted state 7 and a radially expanded state 9. The radially contracted state 7 and radially expanded state 9 are shown in FIG. 2(c). The second member 202 is radially contracted in the radially contracted state 7 and radially expanded in the radially expanded state 9. As the frame moves from the radially contracted state 7 to the radially expanded state 9, the orientation of the second struts 207 changes, causing the first struts 205 to move apart. The orientation of the first struts 205 does not change.

Each of the second struts 207 have a smaller component in the circumferential direction in the radially contracted state 7 than in the radially expanded state 9. The second struts 207 have a larger component in the longitudinal direction in the radially contracted state 7 than in the radially expanded state 9.

Since the second struts 207 extend past the end of the first struts 205 towards the first end of the frame A, the change in orientation of these struts contributes to the change in length of the second member 202. The length of the second member 202 in the radially expanded state 9 is less than the length of the second member 202 in the radially contracted state 9. The change in length of the second member 202 is equal to the change in the longitudinal component of the second struts 207, since the second struts 207 in this case have the same dimensions and are arranged in the same manner. In general, the change in length of the second member 202 is equal to the change in the longitudinal component of the second strut or struts which extend furthest towards the first end of the frame A from the first struts 205.

The change in length of the longitudinal component of a strut between the radially contracted state 7 and the radially expanded state 9 for the general case is illustrated in FIG. 2(c).

The first member 201 comprises a first ring of cells 214 and a second ring of cells 215.

The first ring of cells 214 is formed by third struts 217 and fourth struts 219. Each third strut 217 extends in a direction which has a component in the circumferential direction and is connected at each end through a vertex to the adjacent third strut 217. Each pair of third struts 217 forms a V shape in the longitudinal direction. Third struts 217 form a second ring 221 of struts. The third struts 217 form a zig-zag configuration in the second ring 221, such that every other vertex is displaced from the intervening vertices in the longitudinal direction. The second ring 221 comprises third vertices 210 and fourth vertices 216. The third vertices 210 are closer to the second end of the frame B than the fourth vertices 216.

A third ring of struts 223 is formed by the fourth struts 219. Each fourth strut 219 extends in a direction which has a component in the circumferential direction. Each fourth strut 219 is connected at one end to the fourth vertices 216 between the third struts 217 and at the other end through a fifth vertex 218 to the adjacent fourth strut 219. Thus the fourth vertices 216 each have four struts connected, two third struts 217 and two fourth struts 219. The second ring of struts 221 and the third ring of struts 223 are connected through the fourth vertices 216. The fifth vertices 218 are closer to the first end of the device A than the fourth vertices. Each pair of fourth struts 219 forms a V shape in the longitudinal direction, thus at each fourth vertex 216 the two third struts 217 and two fourth struts 219 form an X configuration, with the third struts 217 extending towards the second end of the frame B and the fourth struts extending towards the first end of the frame A. The fourth struts 219 form a zig-zag configuration.

The second ring of cells 215 is formed by fourth struts 219 and fifth struts 225. A fourth ring of struts 227 is formed by the fifth struts 225. Each fifth strut 225 extends in a direction which has a component in the circumferential direction. Each fifth strut 225 is connected at one end to the fifth vertices 218 between the fourth struts 219 and at the other end through a sixth vertex 220 to the adjacent fifth strut 225. Thus each fifth vertex 218 has four struts connected, two fourth struts 219 and two fifth struts 225. The third ring of struts 223 and the fourth ring of struts 227 are connected through the fifth vertices 218. The fifth vertices 218 are closer to the second end of the device B than the sixth vertices 220. Each pair of fifth struts 225 forms a V shape in the longitudinal direction, thus at each fifth vertex 218 the two fifth struts 225 and two fourth struts 219 form an X configuration, with the fifth struts 225 extending towards the first end of the frame A and the fourth struts extending towards the second end of the frame B. The fifth struts 225 form a zig-zag configuration in the fourth ring 227.

In an embodiment, each cell in the first ring of cells 214 is a quadrilateral shape defined by two third struts 217 and two fourth struts 219. Each cell in the second ring of cells 215 is a quadrilateral shape defined by two fifth struts 225 and two fourth struts 219.

The cells may be diamond shaped for example. Alternatively, the cells may have other shapes.

In an embodiment, there are 12 first struts and 24 of each of the second struts 207, third struts 217, fourth struts 219 and fifth struts 225.

The struts may be straight rod-like shapes, or for example curved shapes. For example, the struts may have an S-shape. The struts may couple with other struts at vertices having simple X or V shapes, or alternatively the vertices may comprise curved U shaped portions such as in the design shown.

The first member thus comprises three rings of struts: the second ring 221, the third ring 223 and the fourth ring 227, each comprising struts extending in a direction having a component in the circumferential directions. These rings are interconnected through vertices, each vertex being connected to two struts from one ring and two struts from the adjacent ring.

When the frame moves from the radially contracted state 7 to the radially expanded state 9, each of the struts extending in a direction having a component in the circumferential direction changes orientation. These struts have a smaller component in the circumferential direction in the radially contracted state 7 than in the radially expanded state 9. These struts have a larger component in the longitudinal direction in the radially contracted state 7 than in the radially expanded state 9. This results in the length of the first member 201 in the radially expanded state 9 being less than the length of the first member in the radially contracted state 7.

The change in length of the first member 201 is equal to the change in the longitudinal component of the third struts 217 plus the change in the longitudinal component of the fourth struts 219 plus the change in longitudinal component of the fifth struts 225. The amount of foreshortening of the first member 201 is equal to the sum of the foreshortening of each ring of struts: the second ring 221, the third ring 223 and the fourth ring 227, because all of these rings are connected through vertices, each vertex being connected to two struts from one ring and two struts from the adjacent ring. In this case, since all the struts having a component in the circumferential direction are the same, the total foreshortening of the first member 201 is equal to the foreshortening of a single strut multiplied by three.

The change in length of the first member 201 between the radially contracted state 7 and the radially expanded state 9 is independent of the change in length of the second member 202 between the radially contracted state and the radially expanded state.

The first end portion 201a of the first member 201 is separate from the second member 202. The first member 201 between the location at which it is coupled to the second member 202 and the first end portion 201a comprises a plurality of vertices between struts having a component in the circumferential direction. As the device moves from the radially expanded state 9 to the radially contracted state 7, the first end portion 201a moves away from the coupling location. This movement does not alter the length of the second member 202.

Since the first ring of struts 213 in the second member 202 is not connected to the rings of struts in the first member 201, the change in length of the first ring of struts 213 is independent of the change in length of the rings of struts in the first member 201.

This means that the change in length of the rings of struts in the first member 201 is not added to the change in length of the first ring of struts 213 in the second member 202 when determining the change in length of the frame.

The second member 202 has one ring of struts, which extends beyond the longitudinal struts 205 at the first end 202a of the second member 202. The first member 201 has three connected rings of struts. The connected rings of struts are connected through vertices between three or more struts extending in a direction which has a component in the circumferential direction. The change in length of each of the connected rings of struts each contributes to the change in length of the first member. The change in length of the first member 201 is greater than the change in length of the second member 202.

Furthermore, since the second member 202 extends beyond the first end portion 201a of the first member 201 at the first end of the frame A and the second end of the frame B extends beyond the first member 201 in the radially contracted state and in the radially expanded state, the change in length of the frame between the radially contracted state 7 and the radially expanded state 9 depends on the change in length of the second member 202 but does not depend on the change in length of the first member 201.

The radial stiffness of the frame is proportional to the number of circumferential rings of struts in the frame. Thus the rings of struts in the first member 201 and the rings of struts in the second member 202 both contribute to the radial stiffness of the frame.

Although in this example, the second member 202 has one ring of struts and the first member 201 has three connected rings of struts, the number of struts in each member may vary. For example, the second member 202 may comprise further rings of struts which are not connected through vertices between three or more struts extending in a direction which has a component in the circumferential direction. In an embodiment, the first member 201 comprises more rings of struts which are inter-connected through vertices between three or more struts extending in a direction which has a component in the circumferential direction than the second member 202.

The first member 201 may be an integral member. The second member 202 may be an integral member. The first member 201 and second member 202 may be integral or may be welded or sutured together for example. Alternatively, they may be coupled by wrapping the struts around one another or bonded together for example.

In an embodiment, the third vertices 210 of the first member 201 are connected to the second end portion 205b of the first struts 205. These are the only locations at which the first member 201 is connected to the second member 202.

The frame further comprises a third member 203. The third member 203 comprises a plurality of sixth struts 231 having a first end portion 231a and a second end portion 231b. The direction from the first end 231a to the second end 231b has a component in the longitudinal direction and is orthogonal to the circumferential direction. The first end portion 231a is closer to the first end of the frame A.

In an embodiment, three of the sixth struts 231c, which are circumferentially spaced equally around the third member 203 have a greater width than the other sixth struts. When the heart valve device is assembled, the leaflets are attached to these wider struts.

Each first strut 205 in the second member 202 is coupled to a sixth strut 231 which is aligned in the longitudinal direction with the first strut 205. In an embodiment, there are 12 first struts and 12 sixth struts.

In an embodiment, the third vertices 210 of the first member 201 are connected to the second end portion 205b of the first struts 205 and the first end portion 231a of the sixth struts 231. In an embodiment, the third struts 217, third vertices 210, first struts 205 and sixth struts 231 are all the same radial distance from the axis and are integral.

In an embodiment, each sixth strut 231 branches at the third vertex 210 into three struts. One of these is the first strut 205, which continues in the longitudinal direction, but curves radially inwardly before the location of the fifth vertex 218 such that it is radially spaced from the fifth vertex 218. The other two struts are the two third struts 217 connected to the third vertex 210. Each of these branch in opposite circumferential directions and towards the first end of the frame A.

The third member 203 further comprises a plurality of seventh struts 233. In an embodiment, there are 24 seventh struts 233. The seventh struts 233 extend in a direction having a component in the circumferential direction. The seventh struts 233 are connected to the sixth struts 231 through seventh vertices 230. Two seventh struts 233 are connected at one end to each sixth strut 231 through a seventh vertex 230. In an embodiment, the seventh struts 233 are connected to the second end portion 231b of the sixth struts 231, but they may be connected at a different location. Each seventh strut 233 is connected at the other end to the adjacent seventh strut 233 at an eighth vertex 232. The seventh struts 233 form a fifth ring of struts 235. Each pair of seventh struts 233 forms a V shape in the longitudinal direction. The seventh struts 233 thus form a zig-zag configuration around the fifth ring 235, such that every other vertex is displaced from the intervening vertices in the longitudinal direction. The seventh vertices 230 are displaced closer to the first end A than the eighth vertices 232.

In this embodiment, the third member 203 comprises the sixth struts 231 and the seventh struts 233, which form a trough shape, i.e. do not define a complete cell. However, in an embodiment, the third member 203 may comprise further struts such that the third member 203 also comprises a plurality of struts defining a plurality of cells. The sixth struts 231, seventh struts 233 and third struts 217 of the first member do form complete cells. Furthermore, the sixth struts 231, seventh struts 233, first struts 205 and second struts 207 form complete cells.

The third member 203 is radially contracted in the radially contracted state 7 and radially expanded in the radially expanded state 9. As the frame moves from the radially contracted state 7 to the radially expanded state 9 the orientation of the seventh struts 233 changes, causing the sixth struts 231 to move apart. The orientation of the fifth struts 231 does not change.

Each of the seventh struts 233 have a smaller component in the circumferential direction in the radially contracted state 7 than in the radially expanded state 9. These seventh struts 233 have a larger component in the longitudinal direction in the radially contracted state 7 than in the radially expanded state 9.

Since the seventh struts 233 extend past the end of the sixth struts 231 towards the second end of the frame B, the change in orientation of these struts contributes to the change in length of the third member 203. The length of the third member 203 in the radially expanded state 9 is less than the length of the third member 203 in the radially contracted state 9. The change in length of the third member 203 is equal to the change in the longitudinal component of the seventh struts 233, since in this case the seventh struts 233 have the same dimensions and the same configuration. In general, the change in length of the third member 203 is equal to the change in the longitudinal component of the seventh strut or struts which extend furthest towards the second end of the frame B from the sixth struts 231.

The second end portion 205b of each first strut 205 is connected to two third struts 217 of the first member 201 and to the first end portion 231a of the aligned sixth strut 231 of the third member 231 through a vertex. The first struts 205 extend towards the first end A of the frame from this vertex and the sixth struts 231 extend towards the second end B of the frame.

The third member 203 extends beyond the first member 201 at the second end of the frame B. The second member 202 extends beyond the first member at the first end of the frame A. The change in length of the frame between the radially contracted state 7 and the radially expanded state 9 thus depends on the change in length of the second member 202 and the third member 203.

Thus when the frame moves from the radially expanded configuration 9 to the radially contracted configuration 7, the longitudinal first struts 205 and sixth struts 231 do not change orientation, they simply move closer together. These struts do not contribute to the change in length of the frame.

There are two outer rings of struts, the first ring 213 at the first end portion 202a of the second member and the fifth ring 235 at the second end portion 203b of the third member 203. Each outer ring comprises struts extending in a direction having a component in the circumferential direction. These struts extend to the end of the frame, and thus the change in orientation of these struts contributes to the change in length of the frame.

The fifth ring 235 is at the second end of the frame B and connected to the longitudinal sixth struts 231. The change in length in the longitudinal direction of this fifth ring 235 changes the distance of the second end of the frame B from the sixth struts 231.

The first ring 213 is at the first end of the frame A and connected to the longitudinal first struts 205, which in turn are connected to the sixth struts 231. The change in length in the longitudinal direction of this first ring 213 changes the distance of the first end of the frame A from the first struts 205.

Thus the change in length of the frame is the change in length in the longitudinal direction of the first ring 213 plus the change in length in the longitudinal direction of the fifth ring 235.

Since the third member 203 extends beyond the first member towards the second end of the frame B and the second member 202 extends beyond the first member towards to first end of the frame A in both the radially contracted state and radially expanded state, the change in length of the first member 201 does not contribute to the change in length of the device.

Furthermore, since the change in length at the first end of the frame A is only dependent on the first ring 213 and the change in length at the second end of the frame B is only dependent on the fifth ring 235, alignment with the native leaflet can be performed on either the upper or the lower edge of the frame.

The first member is coupled to the second member 202 and the third member 203 through longitudinal struts in the second member 202 and the third member 203. The second member 202 and third member 203 together extend the entire length of the frame.

The radial stiffness of the frame is proportional to the number of circumferential rings of struts in the frame. Thus the rings of struts in the first member 201, the rings of struts in the second member 202 and the rings of struts in the third member 203 all contribute to the radial stiffness of the frame. In this case, five rings of struts contribute to the radial stiffness of the frame.

FIG. 2(b) shows the frame in the unwrapped configuration. The first member 201 is shown in darker shading, the second member 202 is shown in medium shading and the third member 203 is shown in light shading. Considering all of the members, a line through the frame in the longitudinal direction will cross a maximum of five struts, as shown by the left line shown in the figure. The radial stiffness is provided by all five rings of struts.

Considering only the third member 203 and the first member 201, a line through the frame in the longitudinal direction will cross a maximum of four struts, as shown by the middle line in the figure.

Considering only the third member 203 and the second member 202 however, a line through the frame in the longitudinal direction will cross a maximum of two struts, as shown by the right line in the figure. These struts are the only struts to contribute to the foreshortening, because the cells in the first member 201 are connected to the second member 202 at each circumferential location at one location along the longitudinal direction, and because the second member 202 is lower, i.e. extends beyond the first member 201 in both the radially expanded state 9 and the radially contracted state 7. In the expanded state, member 202 has a longitudinal length that extends beyond the first member 201 such that the elongation of the first member 201 is encompassed by the second member 202. In other words, the fourth ring 227 doesn't extend beyond the second ring 213 in the contracted state.

The frame may thus maintaining appropriate radial stiffness, with reduced foreshortening.

In an embodiment, the first member 201 and the second member 202 each comprise a ring of struts, each strut in the ring extending in a direction having a component in the circumferential direction. Since rings are divided between the first member 201 and the second member 202, the foreshortening is reduced compared to a device in which all of the rings are in a single member.

The frame comprises dual, connected members, the first member 201 and the second member 202, that reduce foreshortening through the cellular geometry. The change in length between the radially contract state and the radially expanded state is reduced by including two or more layers in the frame which overlap, where one layer extends beyond the other.

The radial stiffness of the frame is maintained, since struts from difference members can also form rings of cells.

A fourth ring of cells 239 at a second end of the device B is formed by a plurality of struts in the third member 203 and a plurality of struts in the first member 201. In other words, the fourth ring of cells 239 is formed by the sixth struts 231 at the second end of the frame B, the seventh struts 233 and the third struts 217. This ring increases the radial stiffness of the frame.

The first member 201 and second member 202 can be manufactured separately, for example by laser cutting from a tube or by additive manufacturing. They can then be welded, bonded, mechanically coupled or sutured together. Alternatively, the first member 201 and second member 202 are integral and are manufactured using additive manufacturing.

The first member 201 and third member 203 may be integral, and the second member 202 welded, bonded, mechanically coupled or sutured for example. Alternatively, the first member 201, second member 202 and third member 203 are integral and are manufactured using additive manufacturing.

In an embodiment, the first member 201 is a stainless steel, titanium or cobalt chromium alloy. In an embodiment, the second member 202 is a stainless steel, titanium or cobalt chromium alloy. In an embodiment, the third member 203 is a stainless steel, titanium or cobalt chromium alloy.

In an embodiment, there is provided an implantable heart valve device, comprising the frame described in relation to FIG. 2 and further comprising a skirt coupled to the frame and a plurality of leaflets. There may be additional components that either support or restrain the leaflets. The skirt may be sutured to the frame and to the leaflets, so that the leaflets are coupled to the frame through the skirt for example.

Table 1 below shows example dimensions for a frame having the design shown in FIG. 2(a):

TABLE 1

| Example dimensions Frame dimensions | |
| --- | --- |
| Uncrimped height | 18.42 mm |
| diameter | 26 mm or 78 Fr |
| Crimped height | 21.5 mm |
| Crimped diameter | 5.5 mm or 16.5 Fr |
| Strut cross section | 0.4 mm by 0.5 mm |

In an embodiment, the strut cross section may be less than 0.4 mm by 0.5 mm, for example the strut cross section may be less than 0.3 mm by 0.4 mm.

Table 2 below shows example dimensions for the parts of a frame having the design shown in FIG. 2(a):

TABLE 2

| Example dimensions Member dimensions | |
| --- | --- |
| First member 201 length | 7.29 mm |
| First member 201 diameter | 26 mm |
| Second member 202 length | 10.89 mm |
| Second member 202 diameter | 24.6 mm |
| Third member 203 length | 7.59 mm |
| Third member 203 diameter | 26 mm |
| First strut 205 length | 8.29 mm |
| First strut 205 diameter | 26 mm-24.6 mm |

Figure 2D:
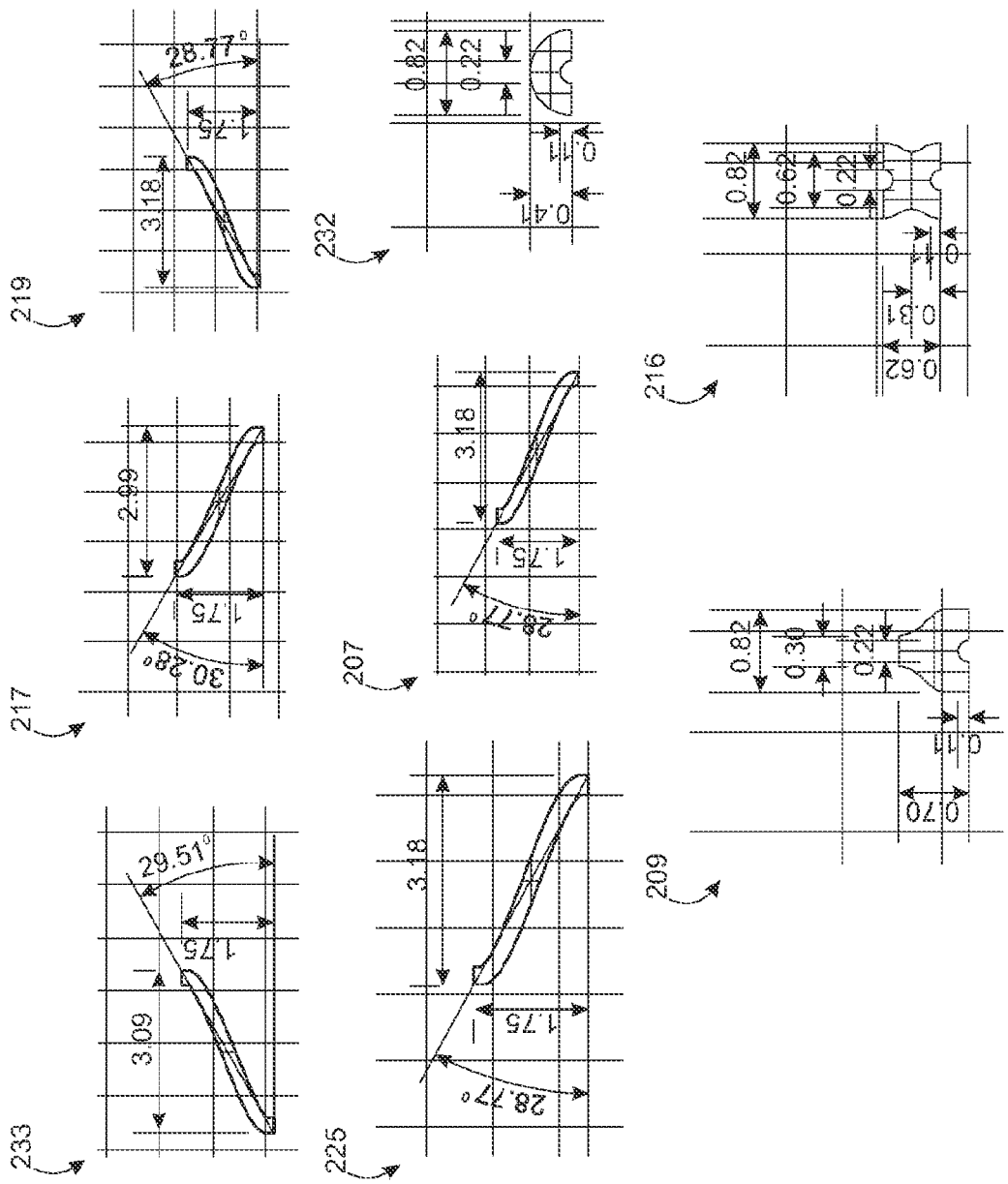
FIGS. 2(d) and 2(e) show example dimensions of the struts of a frame of the design.
Figure 2E:
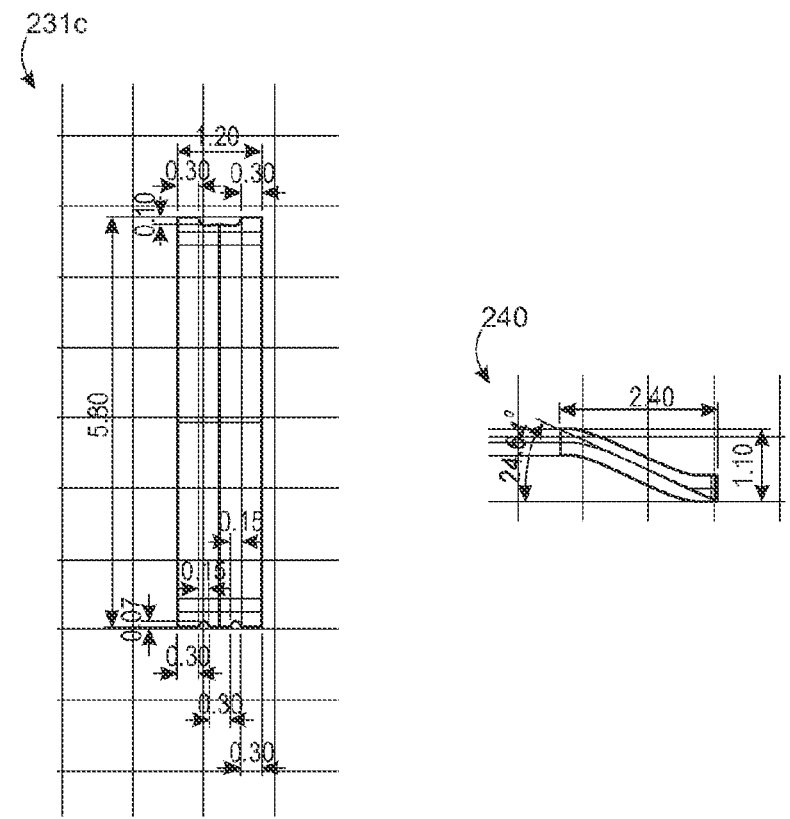

FIGS. 2(d) and 2(e) show example dimensions of the struts of a frame of the design shown in FIG. 2(a).

Figure 3A:
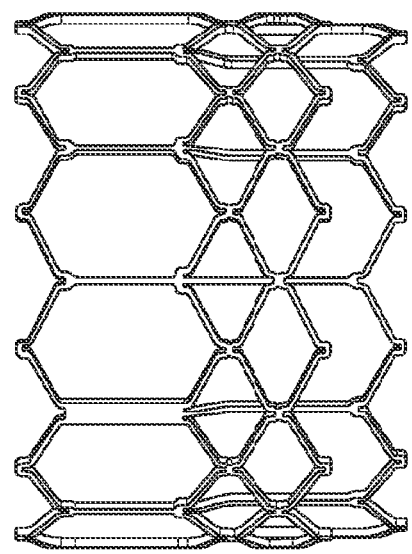
FIG. 3(a) shows a model of a frame in which there are no overlapping members, in the radially expanded and radially contracted state.
Figure 3A:
Figure 3B:
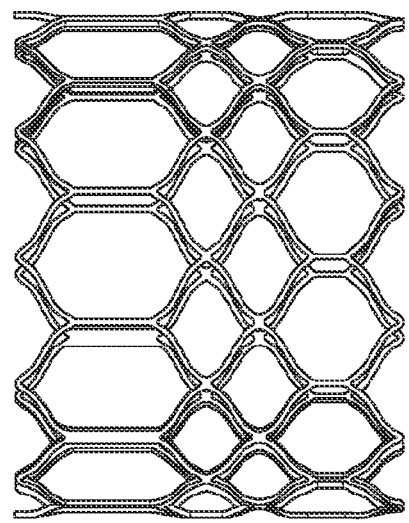
FIG. 3(b) shows a model of a frame in accordance with an embodiment of the present invention.
Figure 3B:

FIG. 3(a) shows a model of a frame in which there are no overlapping members, in the radially expanded and radially contracted state. FIG. 3(b) shows a model of a frame in accordance with an embodiment of the present invention, such as described in relation to FIG. 2(a), i.e. having an overlapping first member and second member in the radially expanded state and the radially contracted state. Both frames comprise four rings of cells and five rings of struts. As can be seen, the increase in length between the radially expanded state and the radially contracted state for the frame of FIG. 3(b) is less than for the frame of FIG. 3(a).

Table 3 below shows the information used to model the frames and the resulting changes in length. The term "open" refers to the radially expanded state and "crimped" refers to the radially contracted state. The diameter is the outer diameter.

TABLE 3

Model information and resulting changes in length

|  | FIG. 3(b) | FIG. 3(a) |
|---|---|---|
| Open Diameter (mm) | 25.2 | 26 |
| Open Height (mm) | 18.42 | 19.97 |
| Crimped Diameter (mm) | 4.1 | 3.86 |
| Crimped Height (mm) | 21.71 | 27.27 |
| Delta radius (mm) | −10.55 | −11.07 |
| Crimped radius as a % of original | 16% | 15% |
| Delta height (mm) | 3.29 | 7.3 |
| Crimped height as a % of original | 118% | 136% |

As can be seen, the modelled device in FIG. 3(b) results in around a 50% reduction in foreshortening from that of FIG. 3(a).

Figure 4:
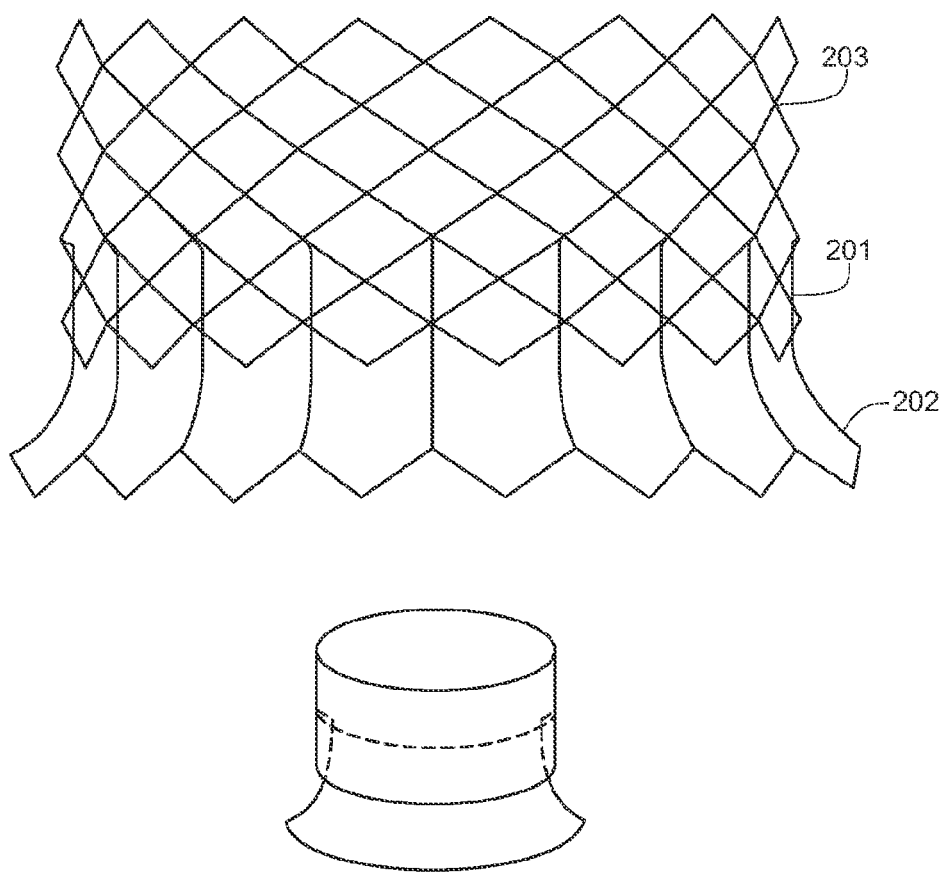
FIG. 4 is a schematic illustration of a frame for an implantable medical device in accordance with a second embodiment of the present invention.

FIG. 4 is a schematic illustration of a frame for an implantable medical device in accordance with a second embodiment of the present invention. The frame may be for an implantable heart valve device for example. The frame according to the second embodiment is the same as the first embodiment except for the third member and including flaring feature in the second member. Therefore, repetition of describing the features which are the same as the first embodiment will be omitted.

In this embodiment, the second member 202 is arranged inside the first member 201. However the first member 201 may be arranged inside the second member 202.

In an embodiment, the second member 202 is formed from a more elastic material than the first member 201 and the third member 203.

In an embodiment, the second member 202 comprises nitinol or is a composite comprising nitinol.

In the second embodiment, the third member 203 comprises five rings of cells. However, the third member 203 may alternatively be the same as the third member 203 of the first embodiment.

The second member is configured 202 to flare radially outwards at a location beyond the first member 201, such that the first end portion 202a of the second member has a radius larger than the first end portion 201a of the first member 201.

This flaring of the second member 202 can reduce paravalvular aortic regurgitation (PAR). PAR can occur after TAVI if an effective seal between the native tissue and the TAVI valve is not made. If there is no effective seal, blood will start leaking around the outside of the valve, and the inside of the tissue. This is referred to as PAR. PAR occurs where the TAVI frame does not shape to the irregular surface of the aortic root. The frames of TAVI devices must be stiff in order to withstand the forces exerted on it by the native tissue. However, this makes the frame less flexible and able to shape around irregular surfaces. PAR can occur particularly when there is a large calcified mass present in the native tissue. Such calcified masses are very hard, unlike the softer tissue about them. As a result, calcified masses can push the frame away from the other tissue, creating a gap between the frame and the tissue.

If PAR occurs, the probability of mortality at one year doubles. Devices have been developed to treat PAR, for instance the SAPIEN 3 device includes a cushion around the outside to plug any holes. However, this increases the complexity of the device.

In an embodiment, the second member 202 comprises less circumferential rings than the first member 201. The second member 202 may comprise less circumferential rings than the third member 203. Thus the first member 201 provides stiffness for resisting the radial forces exerted by the native tissue. However, the second member comprises less rings of struts and thus is extremely malleable. This malleable second member 202 extends beyond the end of the first member 201, and can be used to reduce PAR. The second member 202 flares out at the first end portion 202a. The first member thus has an increasing radius towards the first end portion 202a, such that the radius at the first end portion 202a is greater than the radius of the first member 201 and greater than the radius at the second end portion 202b. The second member 202 may be horn shaped, such as is shown in FIG. 4, i.e. curving outwardly. A portion of the second member 202 including the first end portion 202a acts as an effective seal against the native tissue. The second member 202 acts as a less stiff, inner sub-layer, which flares out to a wider diameter than the first member 201. In this embodiment, each first strut 205 is curved.

In an embodiment, in order to form the flaring of the second member 202, the second member is initially formed in the cylindrical shape. During expansion of the balloon when the device is implanted, the balloon is constricted in the centre, since the first member 201 is much stiffer than either the third member 203 or the second member 202. This creates an hour glass shape in the frame. The third member 203 and second member 202 undergo plastic deformation when the balloon is expanded and therefore retain the shape when the balloon is deflated and removed. In this case, both the second member 202 and third member 203 are flared.

Figure 5:
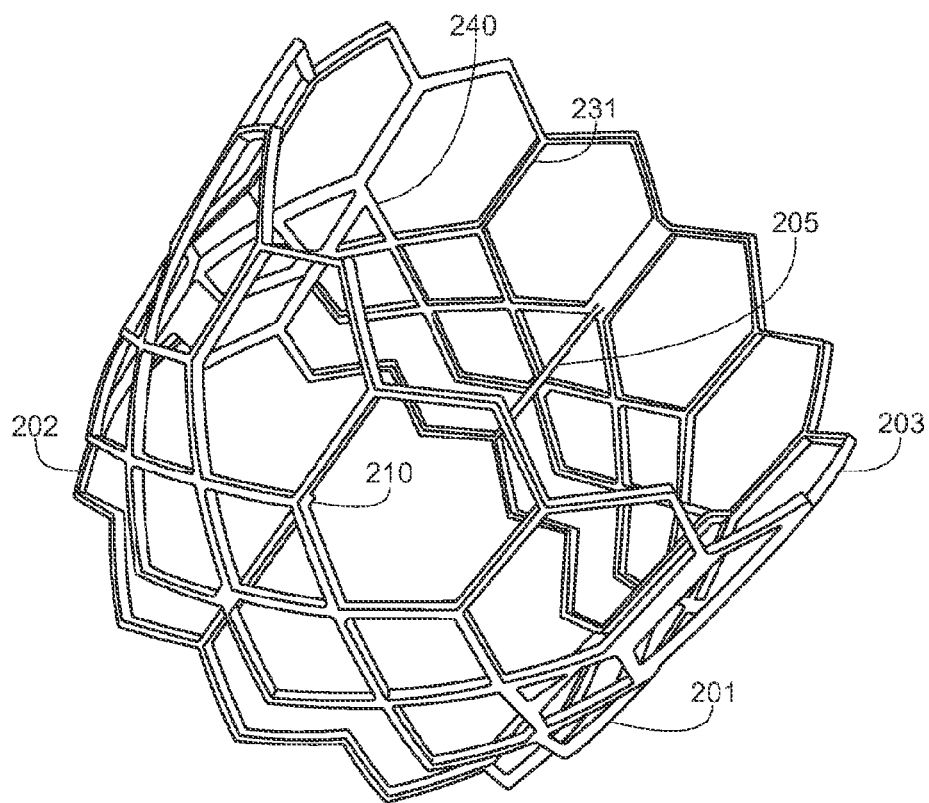
FIG. 5 is a schematic illustration of a frame for an implantable medical device in accordance with a third embodiment of the present invention.

FIG. 5 is a schematic illustration of a frame for an implantable medical device in accordance with a third embodiment of the present invention. The frame may be for an implantable heart valve device for example. The frame according to the third embodiment is the same as the first embodiment except for the configuration of the first struts 205. Furthermore, the struts in this frame are straight rod-like shapes, which connect at simple X or V shaped vertices. Therefore, repetition of describing the features which are the same as the first embodiment will be omitted.

In this embodiment, the frame comprises only six first struts 205. The first struts 205 are connected only to every alternative third vertex 210. Each third vertex 210 of the first member 201 is connected to the first end portion 231a of the sixth struts 231. These third vertices 210 are connected to the first end portion 231a of the sixth struts 231 and the third struts 217. Each sixth strut 231 branches at the third vertex 210 into the two third struts 217 connected to the third vertex 210. Each of these branch in opposite circumferential directions and towards the first end of the frame A.

Every other third vertex 210 is also connected to the second end portion 205b of a first strut 205.

Furthermore, unlike in the first embodiment, in which the third struts 217, third vertices 210, first struts 205 and sixth struts 231 were all at the same radial distance from the axis, in this embodiment, the first struts 205 are coupled to the third vertices 210 by a coupling portion, which extends in a direction having a component in the radial direction. Thus the first struts 205 are radially spaced from the first member 201 along their entire length. The first struts 205 may extend in the longitudinal direction. At these vertices, each sixth strut 231 branches into two struts and a coupling portion. The two struts are the two third struts 217 connected to the third vertex 210. Each of these branch in opposite circumferential directions and towards the first end of the frame A. The coupling portion 240 extends in a direction which has a component in the radial direction, coupling the first member 201 and the second member 202. In this case, the coupling portion 240 extends inwardly, but it may extend outwardly where the second member 202 is arranged outside the first member 201. The coupling portion 240 is connected at one end to the third vertex 210 and at the other end to the second end portion 205b of the first strut 205. It may however be coupled to a different location on the first strut 205 and/or on the third member 203.

The coupling portion may be integral with the second member 202 and/or the first member 201 and/or the third member 203.

Figure 6:
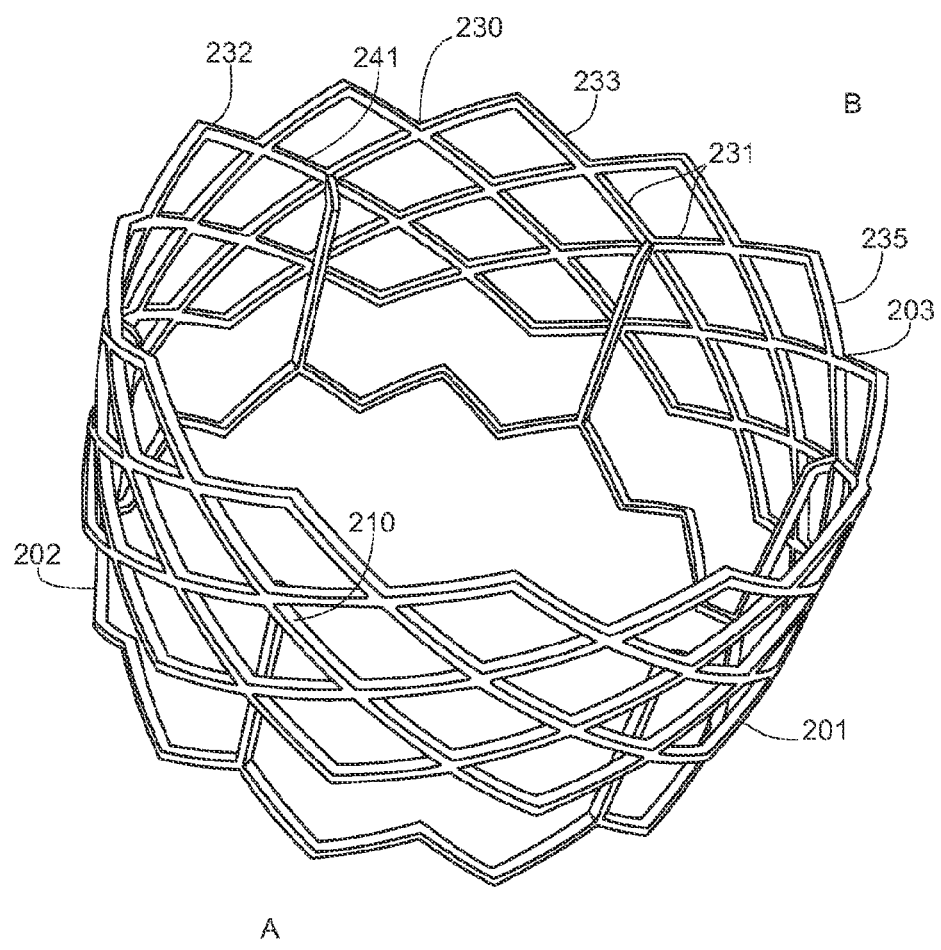
FIG. 6 is a schematic illustration of a frame for an implantable medical device in accordance with a fourth embodiment of the present invention.

FIG. 6 is a schematic illustration of a frame for an implantable medical device in accordance with a fourth embodiment of the present invention. The frame may be for an implantable heart valve device for example. The frame according to the fourth embodiment is the same as the third embodiment except for the configuration of the third member 203. Therefore, repetition of describing the features which are the same as the first embodiment will be omitted.

In this embodiment, the sixth struts 231 extend in a direction having a component in the circumferential direction. Furthermore, there are 24 sixth struts 231. The third member does not comprises any sixth struts 231 of greater width in the frame shown, however the thickness of one or more of the sixth struts 231 may be greater than the others.

Each sixth strut 231 extends in a direction which has a component in the circumferential direction and is connected at one end to a third vertex 210 and at the other end to the adjacent sixth strut 231 through a seventh vertex 230. Each third vertex 210 is connected to two sixth struts 231. Each pair of sixth struts 231 forms a V shape in the longitudinal direction. The sixth struts 231 form a sixth ring 241 of struts. The sixth struts 231 form a zig-zag configuration, such that every other vertex is displaced from the intervening vertices in the longitudinal direction. The second ring 221 comprises third vertices 210 and seventh vertices 230. The third vertices 210 are closer to the first end of the frame A than the seventh vertices 230.

A fifth ring of struts 235 is formed by the seventh struts 233. Each seventh strut 233 extends in a direction which has a component in the circumferential direction. Each seventh strut 233 is connected at one end to the seventh vertices 230 between the sixth struts 231 and at the other end through an eighth vertex 232 to the adjacent seventh strut 233. Thus the seventh vertices 230 each have four struts connected, two sixth struts 231 and two seventh struts 233. The sixth ring of struts 241 and the fifth ring of struts 235 are connected through the seventh vertices 230. The seventh vertices 230 are closer to the first end of the frame A than the eighth vertices 232. Each pair of seventh struts 233 forms a V shape in the longitudinal direction, thus at each seventh vertex 230 the two seventh struts 233 and two sixth struts 231 form an X configuration, with the sixth struts 231 extending towards the first end of the frame A and the seventh struts extending towards the second end of the frame B. The seventh struts 233 form a zig-zag configuration.

The sixth struts 231 and the third struts 217 form a ring of cells which are quadrilateral shapes and each defined by two third struts 217 and two sixth struts 231. The sixth struts 31 and the seventh struts 233 form a further ring of cells which are quadrilateral shape defined by two seventh struts 233 and two sixth struts 231. The cells may be diamond shaped for example.

The third member thus comprises two rings of struts: the sixth ring 242 and the fifth ring 235, each comprising struts extending in a direction having a component in the circumferential directions. These rings are interconnected through vertices to each other and to the first ring 213 in the first member 201, each vertex being connected to two struts from one ring and two struts from the adjacent ring.

The frame thus comprises two outer rings of struts, the first ring 213 at the first end portion 202a of the second member and the fifth ring 235 at the second end portion 203b of the third member 203. Each outer ring comprises struts extending in a direction having a component in the circumferential directions. These struts extend to the end of the frame, and thus the change in orientation of these struts contributes to the change in length of the frame.

The outer rings of struts are connected by the first struts 205 and the coupling portions 240, which extend in directions which do not have a component in the circumferential direction, and thus do not change in orientation between the radially contracted state and the radially expanded state. They are also connected by the sixth struts 231, which in this embodiment do extend in a direction having a component in the circumferential direction, and thus do contribute to the change in length of the frame.

Each of the seventh struts 233 have a smaller component in the circumferential direction in the radially contracted state 7 than in the radially expanded state 9. These seventh struts 233 have a larger component in the longitudinal direction in the radially contracted state 7 than in the radially expanded state 9.

Similarly, each of the sixth struts 231 have a smaller component in the circumferential direction in the radially contracted state 7 than in the radially expanded state 9. These sixth struts 231 have a larger component in the longitudinal direction in the radially contracted state 7 than in the radially expanded state 9.

The change in length of the third member 203 is equal to the change in the longitudinal component of the sixth struts 231 plus the change in the longitudinal component of the seventh struts 233. The amount of foreshortening of the third member 203 is equal to the sum of the foreshortening of each ring of struts: the fifth ring 235 and the sixth ring 242, because these rings are connected through vertices, each vertex being connected to two struts from one ring and two struts from the adjacent ring. In this case, since all the struts having a component in the circumferential direction are the same, the total foreshortening of the third member 203 is equal to the foreshortening of a single strut multiplied by two.

The first ring 213 is at the first end of the frame A and connected to the longitudinal first struts 205, which in turn are connected to the sixth struts 231. The change in length in the longitudinal direction of this first ring 213 changes the distance of the first end of the frame A from the first struts 205.

Thus the change in length of the frame is the change in length in the longitudinal direction of the first ring 213 plus the change in length in the longitudinal direction of the fifth ring 235 and the sixth ring 242, since the first member 201 does not extend beyond the first ring 213 in the contracted state.

Since the third member 203 extends beyond the first member towards the second end of the frame B and the second member 202 extends beyond the first member towards to first end of the frame A, the change in length of the first member 201 does not contribute to the change in length of the device, since the first member 201 does not extend beyond the first ring 213 in the contracted state.

Figure 7A:
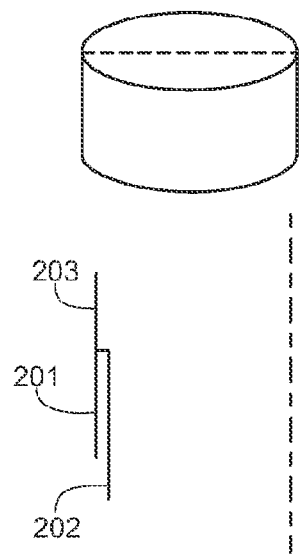
FIGS. 7(a) to (c) are schematic illustrations of example coupling configurations between the first, second and third members.
Figure 7B:
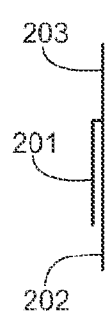
Figure 7C:
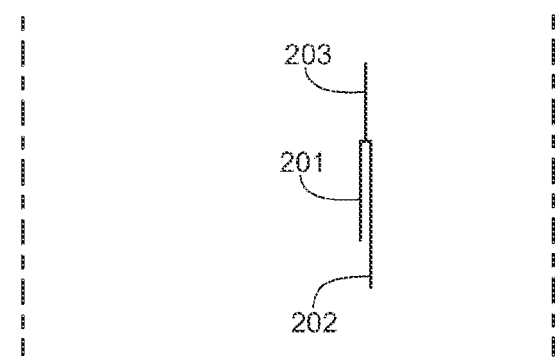

Although in the above described embodiments, the first member 201 and the third member 203 have been coupled at the same radial distance from the axis, as illustrated in FIG. 7(a), in fact, the third member 203 may be coupled to the first member 201 via coupling portions extending in a direction having a component in the radial direction. The first member 201, second member 202 and third member 203 may thus all be radially spaced at the coupling location. Furthermore, the third member 203 may be coupled to the first member 201 at a different location from the location at which the second member 202 is coupled to the first member 201, as illustrated in FIG. 7(b). The second member 202 and the third member 203 may be spaced the same radial distance from the first member 201, as in FIG. 7(b) or a different radial distance. The second member 202 may be coupled to the third member 203 rather than the first member 201 for example. The first member 201 and the second member 202 may both be coupled to the third member 203 through separate coupling portions for example, as shown in FIG. 7(c). In this case, the second member 202 and third member 203 are connected at the same radial location.

Figure 8:
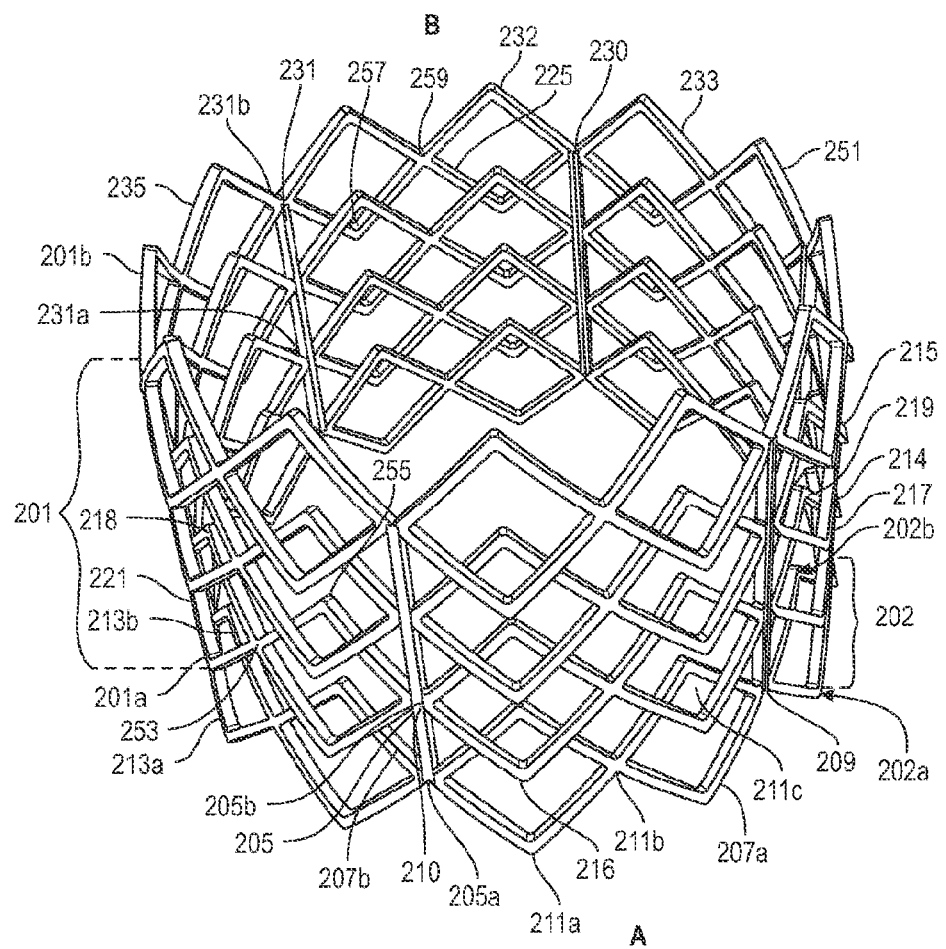
FIG. 8 is a schematic illustration of a frame for an implantable medical device in accordance with a fifth embodiment of the present invention.
Figure 9A:
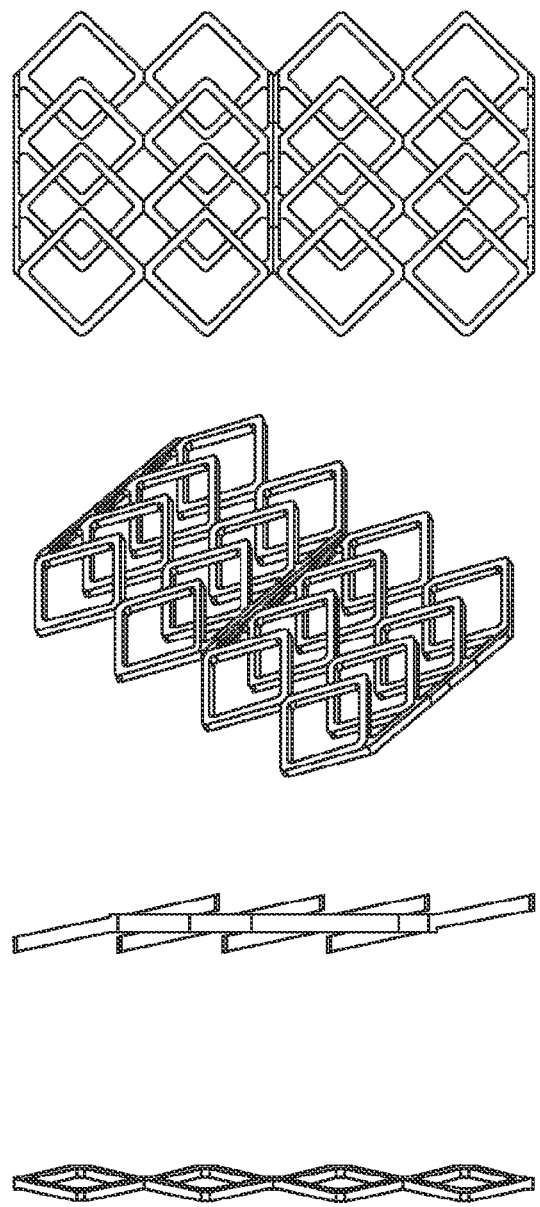
FIG. 9(a) shows an illustration of the frame in an unwrapped configuration and FIG. 9(b) shows example dimensions of an example frame.

FIG. 8 is a schematic illustration of a frame for an implantable medical device in accordance with a fifth embodiment of the present invention. The frame may be for an implantable heart valve device for example. FIG. 9(a) shows an illustration of the frame in an unwrapped configuration.

The frame of FIG. 8 comprises a plurality of rings of cells, connected through struts extending in the longitudinal direction, with no component in the circumferential direction. The cells are not connected through vertices between three or more struts extending in a direction which has a component in the circumferential direction only. In other words, the rings are connected by struts which do not have a component in the circumferential direction. The change in length of each of the rings is thus independent.

The frame comprises a first member 201 and a second member 202. The first member 201 comprises three rings of cells and the second member 202 comprises one ring of cells.

The frame comprises a first end A and a second end B. In an embodiment, the frame is a cylindrical shape.

The first member defines more cells than the second member. In this embodiment, the second member defines 12 cells. In this embodiment, the first member defines 36 cells.

The first member 201 is annular and defines a longitudinal direction which is parallel to the axis of the first member, a radial direction, and a circumferential direction. The first member 201 and the second member 202 are coupled at circumferentially distributed locations.

The first member 201 comprises a first end portion 201a and a second end portion 201b. The first end portion 201a is closer to the first end of the frame A and the second end portion 201b is closer to the second end of the frame B. The second member 202 comprises a first end portion 202a and a second end portion 202b. The first end portion 202a is closer to the first end of the frame A and the second end portion 202b is closer to the second end of the frame B.

The second member 202 overlaps the first end portion 201a of the first member 201 and extends beyond the first end portion 201a of the first member 201. The second member 202 overlaps the first end portion 201a of the first member 201 in the radial direction. The first end portion 202a of the second member 202 is separate from the first end portion 201a of the first member 201.

The first member 201 and the second member 202 have discrete rotational symmetry of the 6th order.

The second member 202 is coupled to the first member 201 at a point part way along the second member 202.

The second member 202 comprises a plurality of first struts 205 having a first end portion 205a and a second end portion 205b. The first end portion 205a is closer to the first end of the frame A and the second end portion 205b is closer to the second end of the frame B. The direction from the first end 205a to the second end 205b has a component in the longitudinal direction and is orthogonal to the circumferential direction.

The second member 202 is coupled to the first member 201 at the second end portions 205b of the first struts 205, which are located at the second end portion 202b of the second member 202. The second member 202 is only coupled to the first member 201 at the second end portions 205b of the first struts 205. The first end portion 205a of the first struts 205 extend beyond the first member 201 in the longitudinal direction.

The second member 202 is annular. Part of the second member 202 is radially displaced from the first member, such that the first member 201 is arranged around the part of the second member 202. Alternatively however, the part of the second member 202 is arranged around the first member 201.

The frame comprises vertices connected between the struts. The vertices are the connection portions between two or more struts. The vertices are hinged portions of the frame. They form the corners, i.e. vertices, of the cells.

The second member 202 comprises a plurality of second struts 207 extending in a direction having a component in the circumferential direction. In this case, the second struts 207 extend in a direction having a component in the longitudinal direction and a component in the circumferential direction.

Two second struts 207a are connected to each first strut 205 through a first vertex 209. In an embodiment, the second struts 207a are connected to the first end portion 205a of the first struts 205 at the first end of the frame A, but they may be connected at a different location. These second struts 207a extend from the first strut 205 in a direction having a component in the longitudinal direction towards the first end of the frame A. Each second strut 207a is connected at the other end to middle second strut 207a, which is in turn connected to another middle second strut 207a, in turn connected to another second strut 207a which is connected to the adjacent first strut 205. Thus there are four connected second struts 207a between each first strut 205, in a zig zag configuration: two second struts each connected to a first strut 205, and two middle second struts which are not connected to a first strut 205. The second struts 207a connected to the first struts 205 are connected to a middle second strut 207a through a second vertex 211a. The middle second struts 207a, i.e. which are not connected to a first strut 205, are connected to each other through a middle second vertex 211b.

The second struts 207a form a first ring of struts 213a. Each pair of second struts 207a forms a V shape in the longitudinal direction. The second struts 207a thus form a zig-zag configuration around the first ring 213, such that every other vertex is displaced from the intervening vertices in the longitudinal direction. The second vertices 211a are displaced closer to the first end A than the first vertices 209 and the middle second vertices 211b.

The second member 202a comprises further second struts 202b. Two further second struts 207b are connected to each first strut 205 through a first vertex 209. In an embodiment, the further second struts 207b are connected to the first end portion 205a of the first struts 205 at the first end of the frame A, but they may be connected at a different location. These further second struts 207b extend from the first end 205a of the first strut 205 in a direction having a component in the longitudinal direction towards the second end of the frame B. Each further second strut 207b is connected at the other end to middle further second strut 207b, which is in turn connected to another middle further second strut 207b, in turn connected to another further second strut 207b which is connected to the adjacent first strut 205. Thus there are four connected further second struts 207b between each first strut 205, in a zig zag configuration: two further second struts 207b each connected to a first strut 205, and two middle further second struts 207b which are not connected to a first strut 205. The further second struts 207b connected to the first struts 205 are connected to a middle further second strut 207b through a further second vertex 211c. The middle further second struts 207b, i.e. which are not connected to a first strut 205, are connected to each other through the middle second vertex 211b. Thus the middle second struts 207a and the middle further second struts 207b are connected through the middle second vertex 211b. Thus between each first strut 205, two cells are formed by the second struts 207, each having a quadrilateral shape.

The further second struts 207b form a second ring of struts 213b. Each pair of further second struts 207b forms a V shape in the longitudinal direction. The further second struts 207b thus form a zig-zag configuration around the second ring 213b, such that every other vertex is displaced from the intervening vertices in the longitudinal direction. The further second vertices 211c are displaced further from the first end A than the first vertices 209 and the middle second vertices 211b.

In this embodiment, the second member 202 comprises 12 cells.

The frame is configured to be radially contracted and expanded, between a radially contracted state 7 and a radially expanded state 9. The second member 202 is radially contracted in the radially contracted state 7 and radially expanded in the radially expanded state 9. As the frame moves from the radially contracted state 7 to the radially expanded state 9, the orientation of the second struts 207 changes, causing the first struts 205 to move apart. The orientation of the first struts 205 does not change.

Each of the second struts 207 have a smaller component in the circumferential direction in the radially contracted state 7 than in the radially expanded state 9. The second struts 207 have a larger component in the longitudinal direction in the radially contracted state 7 than in the radially expanded state 9.

Since the second struts 207a extend past the end of the first struts 205 towards the first end of the frame A, the change in orientation of these second struts 207a contributes to the change in length of the second member 202. The length of the second member 202 in the radially expanded state 9 is less than the length of the second member 202 in the radially contracted state 9.

The first member 201 comprises a second ring of cells 214, a third ring of cells 215 and a fourth ring of cells 251. The first member further comprises a plurality of sixth struts 231 having a first end portion 231a and a second end portion 231b. The direction from the first end 231a to the second end 231b has a component in the longitudinal direction and is orthogonal to the circumferential direction. The first end portion 231a is closer to the first end of the frame A.

Each first strut 205 in the second member 202 is coupled to a sixth strut 231 which is aligned in the longitudinal direction with the first strut 205. In an embodiment, there are 6 sixth struts 231. The second end portion 205b of each first strut 205 is connected to the first end portion 231a of each sixth strut 231 at a third vertex 210.

The second ring of cells 214 is formed by third struts 217 and fourth struts 219. Each third strut 217 extends in a direction which has a component in the circumferential direction and is connected at each end through a vertex to the adjacent third strut 217. Two third struts 217 are connected to each sixth strut 231 through the third vertex 210. Two third struts 217, two fourth struts 219, a first strut 205 and a sixth strut 231 are connected at the third vertex 210. The third struts 217 extend from the third vertex 210 in a direction having a component in the longitudinal direction towards the first end of the frame A. Each third strut 217 is connected at the other end to middle third strut 217, which is in turn connected to another middle third strut 217, in turn connected to another third strut 217 which is connected to the adjacent sixth strut 231 via the third vertex 210. Thus there are four connected third struts 217 between each sixth strut 231, in a zig zag configuration: two third struts 217 each connected to a sixth strut 231, and two middle third struts 217 which are not connected to a sixth strut 231. The third struts 217 connected to the sixth struts 231 are connected to a middle third strut 217 through a fourth vertex 216. The middle third struts 217, i.e. which are not connected to a sixth strut 231, are connected to each other through a fifth vertex 253. The fourth vertices 216 are displaced closer to the first end A than the third vertices 210 and the fifth vertices 253. The third struts 217 form a third ring of struts.

A fourth ring of struts is formed by the fourth struts 219. Two fourth struts 219 are connected to each third vertex and extend in a direction having a component in the longitudinal direction towards the second end of the frame B. Each fourth strut 219 is connected at the other end to a middle fourth strut 219, which is in turn connected to another middle fourth strut 219, in turn connected to another fourth strut 219 which is connected to the adjacent sixth strut 231. Thus there are four connected fourth struts 219 between each sixth strut 231, in a zig zag configuration: two fourth struts 219 each connected to a sixth strut 231, and two middle fourth struts 219 which are not connected to a sixth strut 231. The fourth struts 219 connected to the sixth struts 231 are connected to a middle fourth strut 219 through a sixth vertex 255. The middle fourth struts 219, i.e. which are not connected to a sixth strut 231, are connected to each other through the fifth vertex 253. Thus the middle third struts 217 and the middle fourth struts 219 are connected through the fifth vertex 253. Thus between each sixth strut 231, two cells are formed by the third struts 217 and fourth struts 219, each having a quadrilateral shape.

Each pair of fourth struts 219 forms a V shape in the longitudinal direction. The fourth struts 219 thus form a zig-zag configuration, such that every other vertex is displaced from the intervening vertices in the longitudinal direction. The sixth vertices 255 are displaced further from the first end A than the third vertices 210 and the fifth vertices 253.

The third ring of cells 215 is formed in the same manner. The circumferential struts are connected to the sixth struts 231 at vertices spaced along the sixth struts from the third vertices 210 towards the second end of the frame B.

The fourth ring of cells 251 is formed in the same manner again by fifth struts 225 and seventh struts 233. Each fifth strut 225 extends in a direction which has a component in the circumferential direction. Two fifth struts 225 are connected to each sixth strut 231 through a seventh vertex 230. Two fifth struts 225, two seventh struts 233, and a sixth strut 231 are connected at the seventh vertex 230. The fifth struts 225 extend from the seventh vertex 230 in a direction having a component in the longitudinal direction towards the first end of the frame A. Each fifth strut 225 is connected at the other end to a middle fifth strut 225, which is in turn connected to another middle fifth strut 225, in turn connected to another fifth strut 225 which is connected to the adjacent sixth strut 231 via the seventh vertex 230. Thus there are four connected fifth struts 225 between each sixth strut 231, in a zig zag configuration: two fifth struts 225 each connected to a sixth strut 231, and two middle fifth struts 225 which are not connected to a sixth strut 231. The fifth struts 225 connected to the sixth struts 231 are connected to a middle fifth strut 225 through a sixth vertex 257. The middle fifth struts 225, i.e. which are not connected to a sixth strut 231, are connected to each other through a ninth vertex 259. The sixth vertices are displaced closer to the first end A than the seventh vertices 230 and the ninth vertices 259. The fifth struts 225 form a fifth ring of struts.

A fifth ring of struts 235 is formed by the seventh struts 233. Two seventh struts 233 are connected to each seventh vertex 230 and extend in a direction having a component in the longitudinal direction towards the second end of the frame B. Each seventh strut 233 is connected at the other end to a middle seventh strut 233, which is in turn connected to another middle seventh strut 233, in turn connected to another seventh strut 233 which is connected to the adjacent sixth strut 231. Thus there are four connected seventh struts 233 between each sixth strut 231, in a zig zag configuration: two seventh struts 233 each connected to a sixth strut 231, and two middle seventh struts 233 which are not connected to a sixth strut 231. The seventh struts 233 connected to the sixth struts 231 are connected to a middle seventh strut 233 through a eighth vertex 232. The middle seventh struts 233, i.e. which are not connected to a sixth strut 231, are connected to each other through the ninth vertex 259. Thus the middle fifth struts 225 and the middle seventh struts 233 are connected through the ninth vertex 259. Thus between each sixth strut 231, two cells are formed by the fifth struts 225 and seventh struts 233, each having a quadrilateral shape.

Each pair of seventh struts 233 forms a V shape in the longitudinal direction. The seventh struts 233 thus form a zig-zag configuration, such that every other vertex is displaced from the intervening vertices in the longitudinal direction. The eighth vertices 232 are displaced further from the first end A than the seventh vertices 230 and the ninth vertices 259.

The first member 201 is radially contracted in the radially contracted state 7 and radially expanded in the radially expanded state 9. As the frame moves from the radially contracted state 7 to the radially expanded state 9 the orientation of the seventh struts 233 and fifth struts 225 changes, causing the sixth struts 231 to move apart. The orientation of the sixth struts 231 does not change.

Each of the seventh struts 233 have a smaller component in the circumferential direction in the radially contracted state 7 than in the radially expanded state 9. These seventh struts 233 have a larger component in the longitudinal direction in the radially contracted state 7 than in the radially expanded state 9.

Since the seventh struts 233 extend past the end of the sixth struts 231 towards the second end of the frame B, the change in orientation of these struts contributes to the change in length of the first member 201 and of the frame. The length of the first member 201 in the radially expanded state 9 is less than the length of the first member 201 in the radially contracted state 9.

The first member 201 extends beyond the second member 202 at the second end of the frame B. The second member 202 extends beyond the first member 201 at the first end of the frame A. The change in length of the frame between the radially contracted state 7 and the radially expanded state 9 thus depends on the change in length of the second member 202 at the first end of the frame A and the first member 201 at the second end of the frame B. The second end of the first member 201b extends beyond the second end of the second member 202b. The first end of the second member 202a extends beyond the first end of the first member 201a.

Thus when the frame moves from the radially expanded configuration 9 to the radially contracted configuration 7, the longitudinal first struts 205 and sixth struts 231 do not change orientation, they simply move closer together. These struts do not contribute to the change in length of the frame.

There are two outer rings of struts, the first ring 213a at the first end portion 202a of the second member and the fifth ring 233 at the second end portion 203b of the first member 201. Each outer ring comprises struts extending in a direction having a component in the circumferential directions. These struts extend to the end of the frame, and thus the change in orientation of these struts contributes to the change in length of the frame.

The fifth ring 235 is at the second end of the frame B and connected to the longitudinal sixth struts 231. The change in length in the longitudinal direction of this fifth ring 235 changes the distance of the second end of the frame B from the sixth struts 231.

The first ring 213a is at the first end of the frame A and connected to the longitudinal first struts 205, which in turn are connected to the sixth struts 231. The change in length in the longitudinal direction of this first ring 213a changes the distance of the first end of the frame A from the first struts 205.

Thus the change in length of the frame is the change in length in the longitudinal direction of the first ring 213a plus the change in length in the longitudinal direction of the fifth ring 235.

Since the other rings of struts in the first member 201 and the second member 202 are connected to the outer rings only through struts which do not have a component in the circumferential direction, the change in length of these rings does not contribute to the change in length of the frame.

Furthermore, since the change in length at the first end of the frame A is only dependent on the first ring 213a and the change in length at the second end of the frame B is only dependent on the fifth ring 235, alignment with the native leaflet can be performed on either the upper or the lower edge of the frame.

The radial stiffness of the frame is proportional to the number of circumferential rings of struts in the frame. In this case, eight rings of struts contribute to the radial stiffness of the frame.

The first member 201 and second member 202 can be manufactured separately, for example by laser cutting from a tube or by additive manufacturing. They can then be welded, bonded, mechanically coupled or sutured together. Furthermore, each ring in the first member could be manufactured separately for example. Alternatively, the first member 201 and second member 202 are integral and are manufactured using additive manufacturing.

Although in this example, the second member 202 has two rings of struts and the first member 201 has six rings of struts, the number of struts in each member may vary.

Figure 9B:
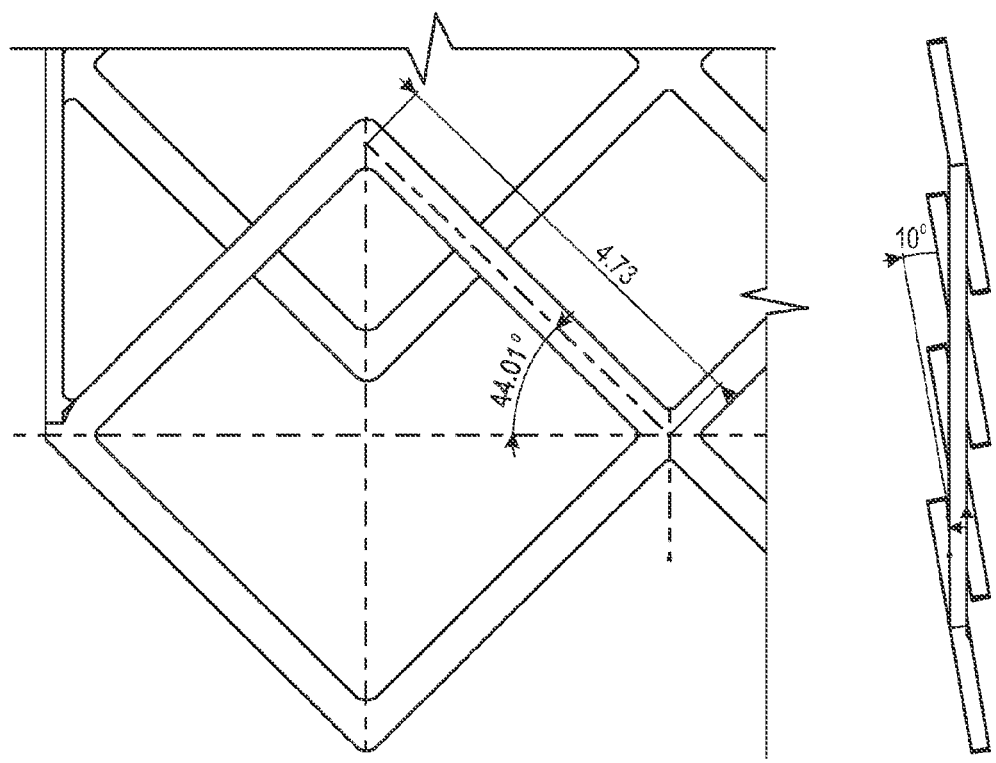

FIG. 9(b) shows example dimensions of an example frame of the design shown in FIG. 8. All the cells in the frame may be the same dimensions. The diameter of the example frame is 29 mm and the height is 20 mm.

The frame design illustrated in FIG. 8 may be adapted for use in a stent for example. A frame for a stent is longer than the frame shown in FIG. 8, and may therefore comprise further repetitions of the rings of cells. A stent frame may be around 100 mm in height for example. The frame may have a similar diameter or a different diameter, for example it may comprise more or less cells in each ring.

Figure 10:
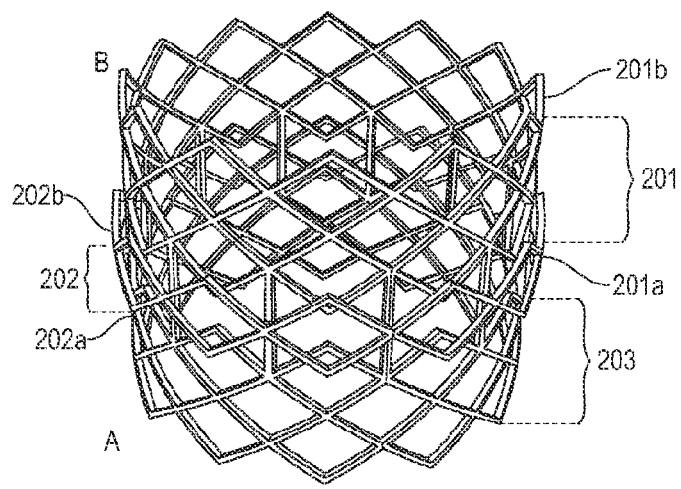
FIG. 10 is a schematic illustration of a frame for an implantable medical device in accordance with a sixth embodiment of the present invention
Figure 10:
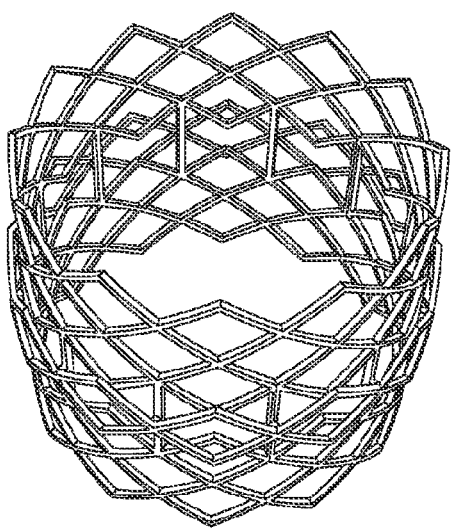
Figure 11A:
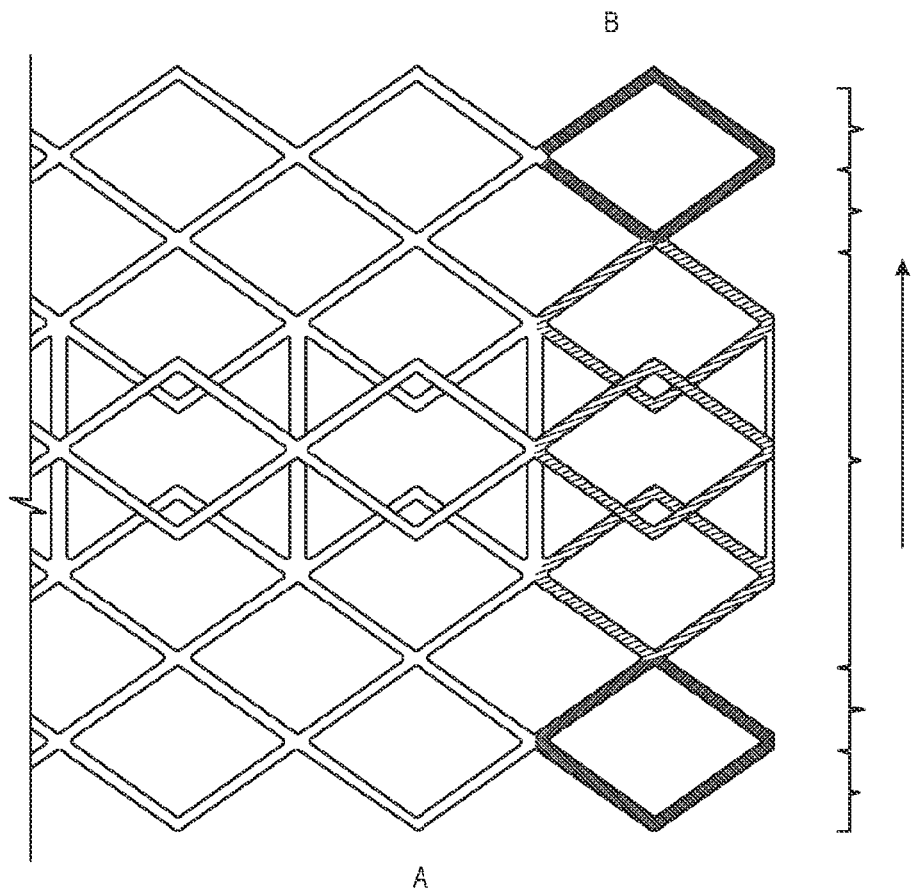
FIGS. 11(a) to (c) show an illustration of the frame in an unwrapped configuration.
Figure 11B:
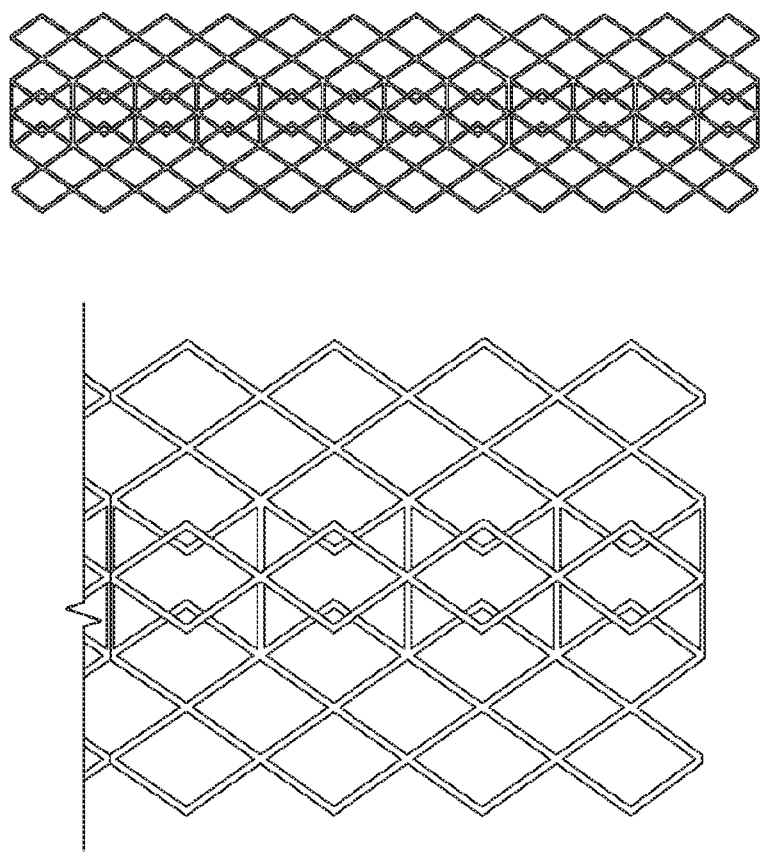
Figure 11C:
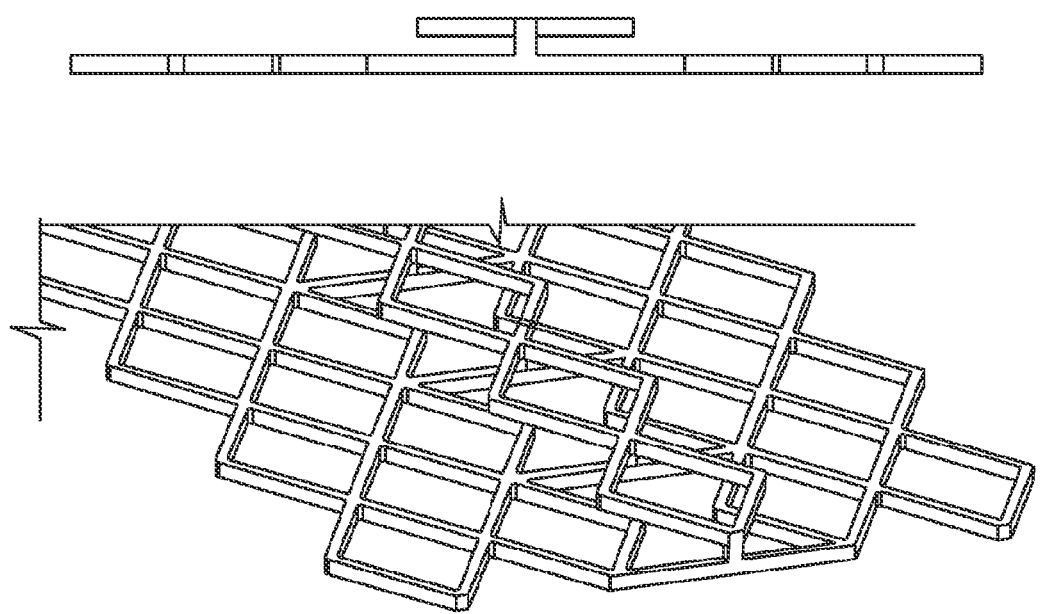

FIG. 10 is a schematic illustration of a frame for an implantable medical device in accordance with a sixth embodiment of the present invention. The frame may be for an implantable heart valve device for example. FIGS. 11(*a*) to (*c*) show an illustration of the frame in an unwrapped configuration. The frame according to the sixth embodiment is similar to the fifth embodiment except that it includes a third member 203 and the rings of cells of the first member 201 are connected through vertices between struts with components in the longitudinal direction. Therefore, repetition of describing the features which are the same as the fifth embodiment will be omitted.

This design allows control of the foreshortening in a specific part of the frame, in this case in the middle of the frame.

In the direction of the arrow in FIG. 11, each strut will move when being crimped/expanded relative to the midpoint of the frame, which is considered fixed. The extent to which the struts move is dependent on the number of struts having a component in the circumferential direction through which they are connected to the mid-point of the frame A. For the middle three cells, each strut moves relative to the mid-point only by its own angular rotation, since it is connected to the mid-point directly or through struts which do not have a component in the circumferential direction. The next pairs of struts move due to their own angular rotation and the strut below, since they are connected to the mid-point of the frame through a single extra strut having a component in the circumferential direction. The next pairs of struts move due to their own angular rotation and the two struts below, since they are connected to the mid-point of the frame through two extra struts having a component in the circumferential direction. There is thus a large band in the centre of the frame that suffers very little foreshortening. This may reduce the incidence of debris release.

In this frame, the first member 201 comprises three rings of cells, each connected through vertices connected to three or more struts having a component in the circumferential direction, as for the first member described in relation to FIG. 2*a*. There are four rings of struts. The second member 202 comprises a single ring of cells, which is connected to the first member 201 through a plurality of struts extending in a direction which does not have a component in the circumferential direction. In this case they extend in the longitudinal direction. There are two rings of struts.

In this embodiment, the second member 202 defines 12 cells. In this embodiment, the first member defines 36 cells.

The first member 201 is annular and defines a longitudinal direction which is parallel to the axis of the first member, a radial direction, and a circumferential direction. The first member 201 and the second member 202 are coupled at circumferentially distributed locations.

The first member 201 comprises a first end portion 201*a* and a second end portion 201*b*. The first end portion 201*a* is closer to the first end of the frame A and the second end portion 201*b* is closer to the second end of the frame B. The second member 202 comprises a first end portion 202*a* and a second end portion 202*b*. The first end portion 202*a* is closer to the first end of the frame A and the second end portion 202*b* is closer to the second end of the frame B.

The second member 202 overlaps the first end portion 201*a* of the first member 201 and extends beyond the first end portion 201*a* of the first member 201. The second member 202 overlaps the first end portion 201*a* of the first member 201 in the radial direction. The first end portion 202*a* of the second member 202 is separate from the first end portion 201*a* of the first member 201.

The third member also comprises three rings of cells, each connected through vertices connected to three or more struts having a component in the circumferential direction, as for the first member described in relation to FIG. 2*a*. The second member 202 is connected to the third member 203 through the plurality of struts extending in a direction which does not have a component in the circumferential direction. There are four rings of struts.

When the frame moves from the radially contracted state 7 to the radially expanded state 9, each of the struts extending in a direction having a component in the circumferential direction changes orientation. These struts have a smaller component in the circumferential direction in the radially contracted state 7 than in the radially expanded state 9. These struts have a larger component in the longitudinal direction in the radially contracted state 7 than in the radially expanded state 9. This results in the length of the frame in the radially expanded state 9 being less than the length of the first member in the radially contracted state 7.

The change in length of the first member 201 is equal to the change in the longitudinal component of each of the four rings of struts, because all of these rings are connected through vertices, each vertex being connected to two struts from one ring and two struts from the adjacent ring. In this case, since all the struts having a component in the circumferential direction are the same, the total foreshortening of the first member 201 is equal to the foreshortening of a single strut multiplied by four.

The change in length of the third member 203 is also equal to the change in the longitudinal component of each of the four rings of struts, because all of these rings are connected through vertices, each vertex being connected to two struts from one ring and two struts from the adjacent ring. In this case, since all the struts having a component in the circumferential direction are the same, the total foreshortening of the third member 203 is equal to the foreshortening of a single strut multiplied by four.

The change in length of the first member 201 between the radially contracted state 7 and the radially expanded state 9 is independent of the change in length of the second member 202 between the radially contracted state and the radially expanded state.

The first end portion 201*a* of the first member 201 is separate from the second member 202. As the device moves from the radially expanded state 9 to the radially contracted state 7, the first end portion 201*a* relative to the second member 202. This movement does not alter the length of the second member 202.

Since the rings of struts in the second member 202 are not connected to the rings of struts in the first member 201 through struts having a component in the circumferential direction, the change in length of the rings of struts in the second member 202 is independent of the change in length of the rings of struts in the first member 201.

This means that the change in length of the rings of struts in the first member 201 is not added to the change in length of the second member 202 when determining the change in length of the frame.

The first member 201 extends beyond the second member 202 at the first end of the frame B. The third member 203 extends beyond the second member 202 at the first end of the frame A. The change in length of the frame between the radially contracted state 7 and the radially expanded state 5 thus depends on the change in length of the second member 202 and the third member 203, but not the second member 202.

The radial stiffness of the frame is proportional to the number of circumferential rings of struts in the frame. Thus the rings of struts in the first member 201, the rings of struts in the second member 202 and the rings of struts in the third member 203 all contribute to the radial stiffness of the frame.

The frame shown in FIGS. 10 and 11 provides local foreshortening in the centre of the frame which is different to the foreshortening at the ends of the frame. Since the second member 202 foreshortens only by the amount of a single ring, as do the adjacent rings, there is minimal central foreshortening. This may reduce stress on tissue during deployment as the shear is reduced at the tissue surface, which may reduce the rate of plaque rupture.

Figure 12:
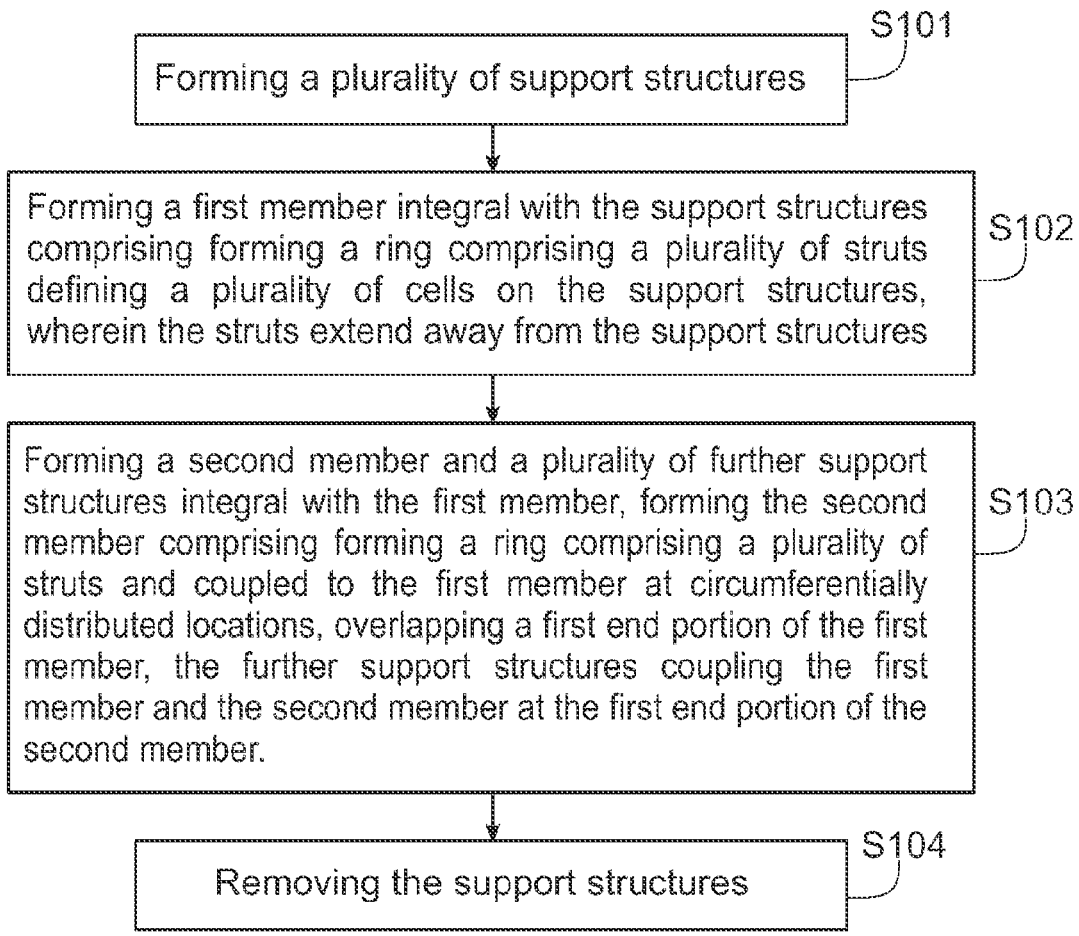
FIG. 12 shows a flow chart illustrating a method of manufacturing a frame for an implantable medical device.

FIG. 12 shows a flow chart illustrating a method of manufacturing a frame for an implantable medical device, comprising forming a plurality of struts defining a plurality of cells by additive manufacturing. The frame may be for an implantable heart valve device for example.

The method may be used to manufacture a frame for a valve configured for surgical implantation or for transcatheter implantation.

In an embodiment, the frame is formed using metal sintering. The frame may be formed using direct metal laser sintering (DMLS). The DMLS may be selective laser sintering (SLS) for example, which is a specific additive manufacturing method using metallic powder as the material which forms the frame.

The metallic material used to form the struts may be a stainless steel, titanium or cobalt chromium alloy for example. The metallic material used to form the struts may be one or more of the following materials:
CL 20ES—stainless steel
CL 30AL—aluminium alloy
CL 31AL—aluminium alloy
CL 41Ti—titanium alloy
CL 42Ti—titanium alloy
CL 50WS—hot work steel
CL 80CU—Bronze alloy
CL 91RW—stainless hot work steel
CL 92PH—stainless precipitation hardening steel
CL 100NB—Nickel alloy
CL 101NB—Nickel alloy
Remanium star CL—cobalt chromium alloy
Remanium CL In an embodiment, the entire frame is integral and is formed in a single additive manufacturing process. Manufacturing the frame in this manner allows many different cell and frame geometries to be formed, and offers cheaper and faster manufacturing.

Additive manufacturing may be performed by a 3D printer. 3D printers may read inputted data files which contain a code that specifies the location of the frame material in each layer, the direction in which the laser spot is moved, and the speed to which the laser spot moves. The file may comprise further information. The input data file can be specific to a particular printer, such that only the specific printer can read it, or it can be more general, such as files based on the g-code format.

A CAD (computer aided design) model of the frame may be produced initially. This may then be converted into a printer input file. The printing file may comprise information indicating the orientation in which the frame should be printed, and information indicating any support structures, as well as the information from the CAD file. The printing file is then inputted into a 3D printer which processes it and begins printing.

Manufacture of the frame involves producing thin lines or tubes of material. These lines can be used to form planes or layers, which are layered to form the frame. The thickness of each layer depends on the height of the lines. Generally, all of the planes are parallel.

The 3D printer may comprise a print bed, onto which the frame is formed. Initially, the print bed is covered in a thin layer of the printing material, the height of a single layer. The laser is then directed at the areas of the layer of material in which the frame is to be formed for the particular layer. The laser is directed at only these areas. Solid material is formed in the areas at which the laser was directed for the layer. The other parts of the layer remain a powdered material. The print bed then lowers by the height of a single layer, and the process is repeated. In this way, the frame is built up layer by layer, with the laser forming the parts of the frame in each layer.

The method may include v-shift of the printing apparatus, in which the print plate changes its vertical position, towards or away from the laser focal point whilst the material is deposited. This can improve the surface texture.

The method may comprise printing the frame from a first end of the frame to a second end of the frame, i.e. building up the frame from layers from a first end to a second.

A plurality of support structures may be formed initially on the print bed. The support material is formed initially so that when the piece is removed from the print bed, the support is cut, not the frame. The support structures anchor the frame to the print bed during printing.

Figure 13A:
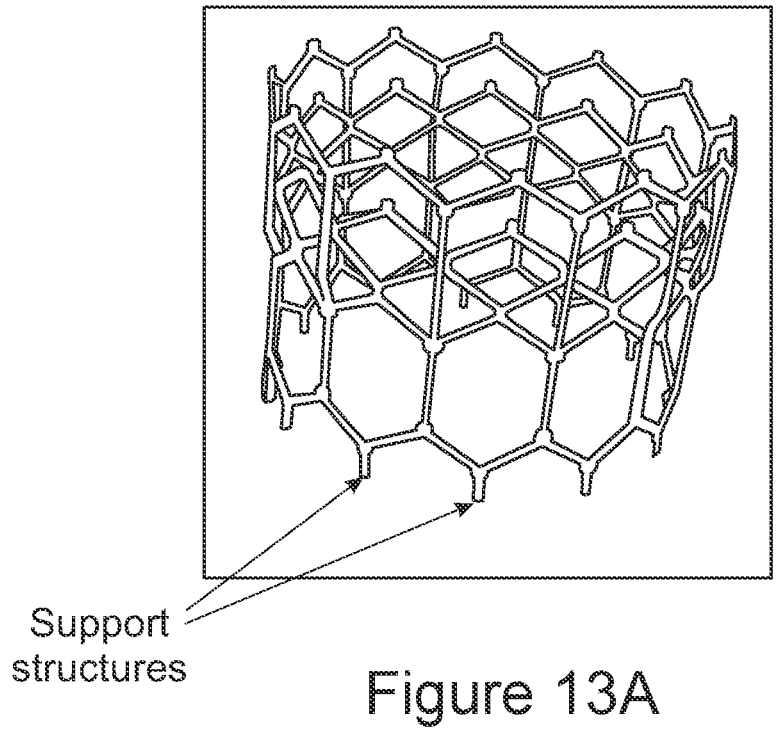
FIGS. 13 and 14 show photographs of frames together with the support structures.
Figure 13B:
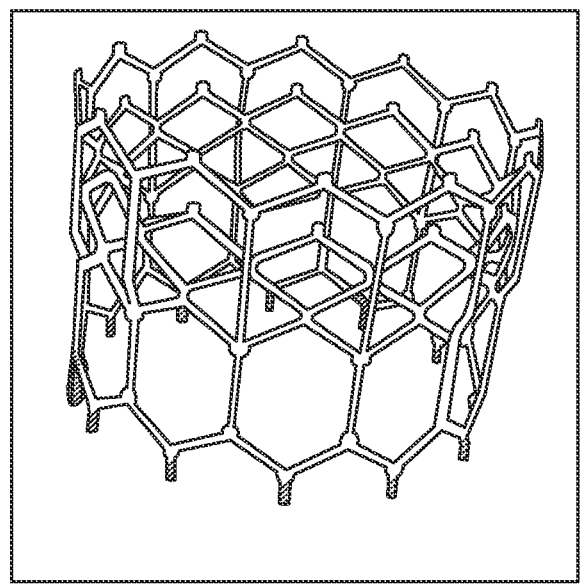

In S101, a plurality of support structures are formed. A photograph of the frame together with the support structures is shown in FIG. 13. The support structures may each be column-shaped or rectangular shaped, extending vertically up from the print bed. Rectangular shaped support structures may have rounded corners. In an embodiment, the support structures may have a width of 1.1 mm and a height of 4.5 mm. There may be 12 support structures formed on the print bed. The support structures may be equally spaced around a ring. Each support structure is formed by directing the laser on an area corresponding to the cross-sectional slice of the support structure on each successive layer, and building up the support structure column layer by layer.

In an embodiment, the cross sections of the support structures are cross shaped.

In an embodiment, the support structures are tapered, for example they may have an inverted cone shape.

The support structures may be configured such that the surface area of support structure material in direct contact with the frame is minimized, in order to facilitate removal.

The struts of the frame are then formed on the support structures and integral with the support structures. In this embodiment, a frame such as described in relation to FIG. 2a, and such as shown in FIG. 13 is formed, thus the method is described specifically for such a frame. However, in general, the struts are formed layer by layer upwards from the support structures. The struts extend away from the support structures.

In S102, the first member 201 is formed integral with the support structures. This comprises forming a ring comprising a plurality of struts on the support structures, wherein the struts extend away from the support structures. In an embodiment, this step comprises forming the third member 203 directly on and integral with the support structures, and forming the first member 201 on and integral with the third member 203.

In an embodiment, two seventh struts 233 are formed layer by layer on each support structure. Each extends in a direction having a component in the vertical direction away from the print bed and a component in the circumferential direction. For each support structure, each seventh strut 233 extends in an opposite circumferential direction. The seventh struts 233 are integrally formed at one end with the top of the support structure and with the other seventh strut 233 on the support structure, forming an eighth vertex 232. Each seventh strut 233 is integrally formed at the other end with an end of the adjacent seventh strut 233, forming a seventh vertex 230. The adjacent seventh strut 233 is integral at its other end with the adjacent support structure. In this way the ring of seventh struts 233 is formed.

The sixth struts 231 are then formed layer by layer from the seventh vertices 232, in the vertical direction away from the print bed.

The first member 201 and second member 202 are then formed on top of and integral with the sixth struts 231. However, it is understood that the device may not include the third member 203, and the first member 201 and/or second member 202 formed directly on the support structures for example.

The first member is formed by forming a first ring comprising a plurality of struts on and integral with the sixth struts 231, wherein the struts extend away from the sixth struts 231. In an embodiment, this comprises forming the third struts 217, fourth struts 219 and fifth struts 225 described in relation to FIG. 2a above, layer by layer. These struts define a plurality of cells, and form an annular first member.

The second member 202 is formed in parallel with the first member 201, i.e. at the same time as the first member 201, in S103. The first struts 205 of the second member are formed on and integral with the sixth struts 231, extending away from the sixth struts 231 in the vertical direction. The first struts may extend in a direction with a component in the radial direction or there may be a radial coupling portion formed between the sixth struts 231 and the first struts 205 for example. The first member 201 and the second member 202 are integrally joined at the locations of the sixth struts 231, i.e. at circumferentially distributed locations.

Part of the second member 202 in this case is formed inside the first member 201 in the radial direction, however it may instead be formed outside the first member 201.

The second member overlaps a first end portion 201a of the first member 201 and extends beyond the first end portion 201a of the first member 201 in the longitudinal direction. This means that the second member 202 continues to be formed past the end of the first member 201.

In an embodiment, the radial spacing between the first member 201 and the second member 202 is 40 micron or more at the first end portion 201a of the first member. This avoids fusion between the two members. In an embodiment the radial spacing is greater than 100 microns.

Figure 14A:
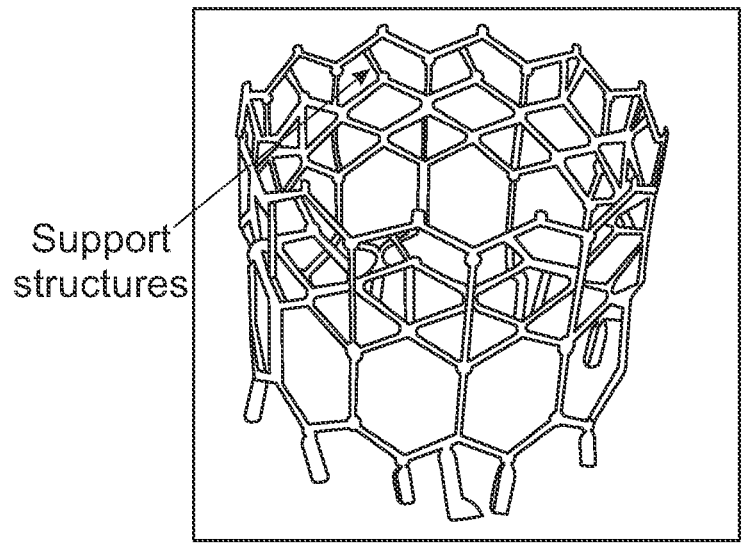
Figure 14B:
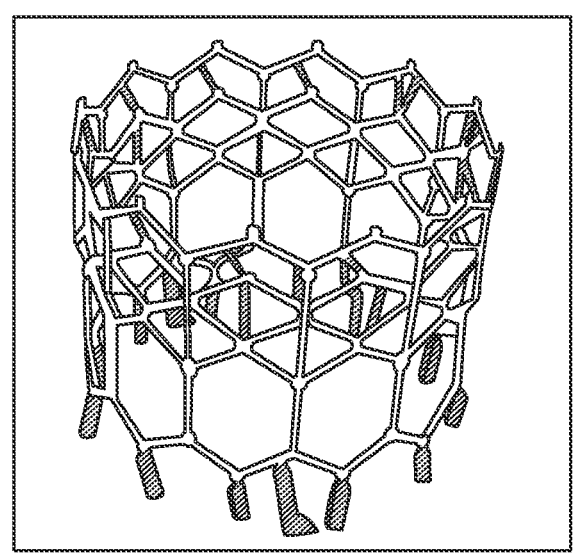

A plurality of further support structures may also be formed between the first member 201 and the second member 202 at the first end portion 201a of the first member 201. This provides further support for the two members. A frame together with these extra support structures is shown in FIG. 14. These may be formed between the sixth vertices and the second struts 207 for example. These support structures may be formed to support the second member 202.

Once the frame has been formed it is removed from the 3D printer and cut away from the base at the lower part of the support structure.

The support structures are then removed from the frame. This may be done by electro-polishing or mechanical cutting for example. Electro-polishing may be used since it removes material on all exposed surfaces and enhances the surface finish of the frame. It can be used to remove the support structures. The junction between the support structures and the frame has a width below a threshold value such that the electro-polishing process separates the support structure from the frame.

Further processing may be performed on the frame, for instance CNC machining or electro-polishing to smooth the frame.

Although in the method described, the entire frame is formed in a single process, as an integral piece, alternatively separate parts of the frame may be manufactured separately by additive manufacturing and the parts welded, bonded, mechanically coupled or sutured together.

In an embodiment, the frame is formed from two or more different materials, for example different alloys. In an embodiment, all or part of the frame is formed from fibre embedded composites. The frame can be manufactured from different materials using additive manufacturing, or by post-processing, for example forming different parts separately from different materials and then suturing or welding the parts together. For example, different materials may be printed in the same process, at the same time.

In an embodiment, the medical device is formed by additive manufacturing, using metal sintering for the frame and polymer printing for the leaflets. The frame and leaflets may be printed separately for example and then bonded or sutured together.

Figure 15:
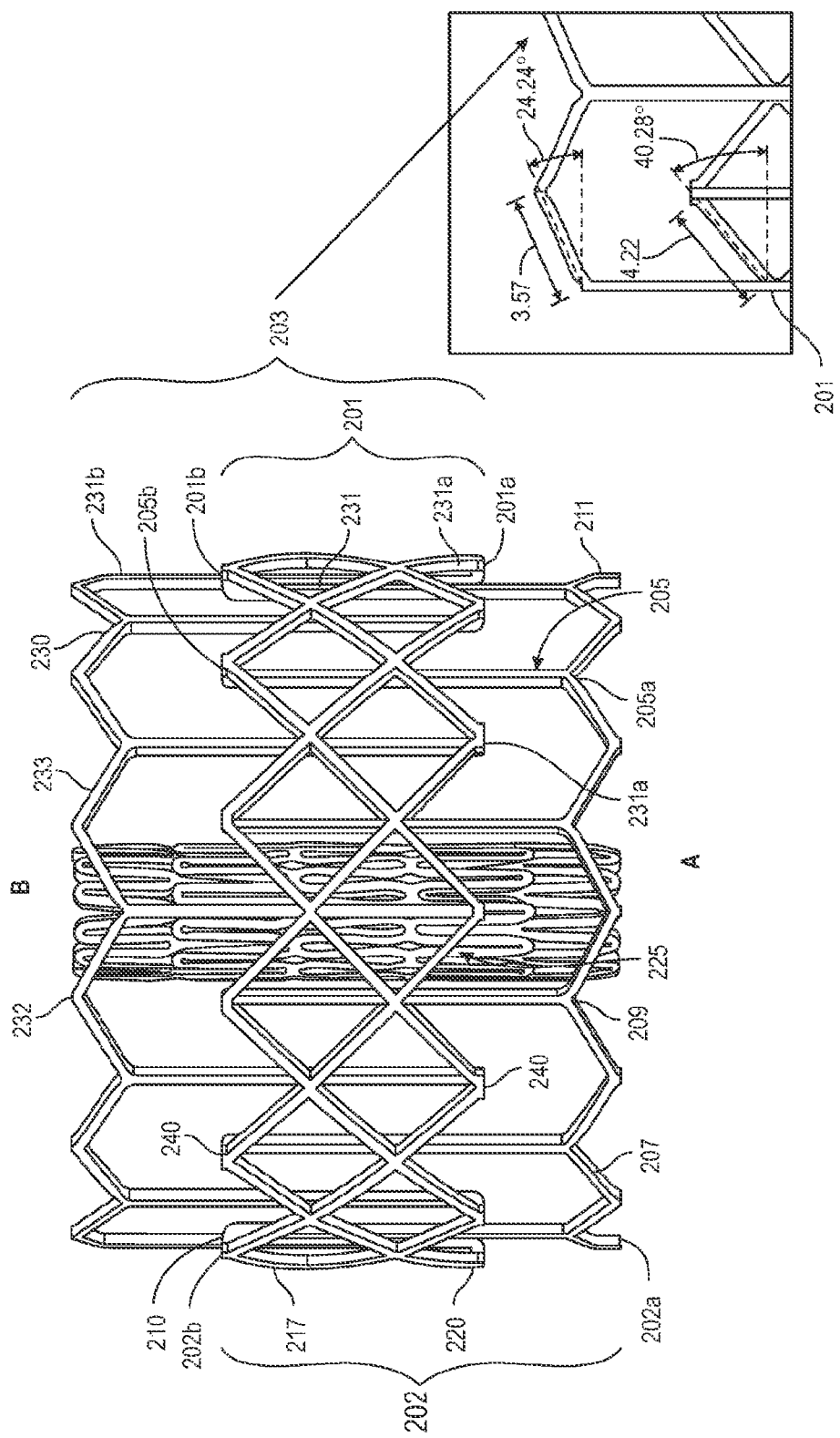
FIG. 15 is a schematic illustration of a frame for an implantable medical device in accordance with a seventh embodiment of the present invention.
Figure 16A:
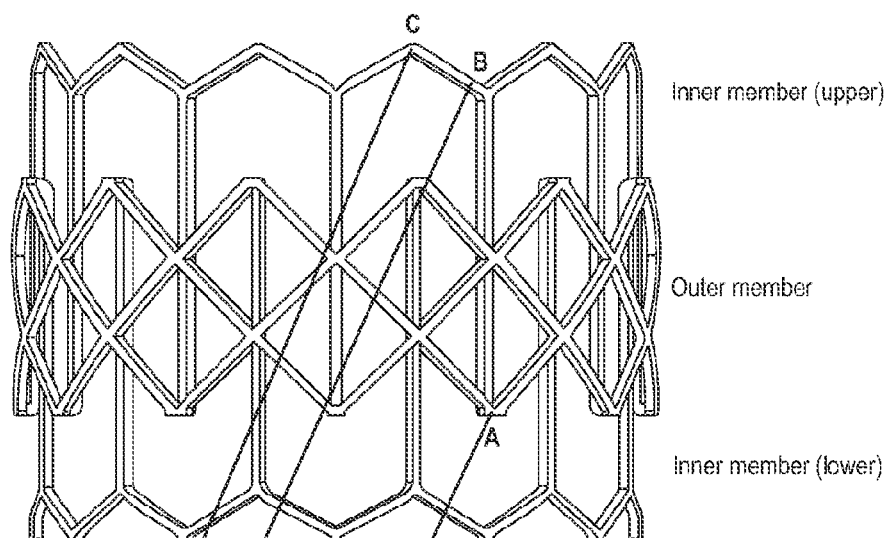
FIGS. 16(a) and 16(b) show schematic illustrations of the frame in an expanded configuration and a crimped configuration.
Figure 16B:
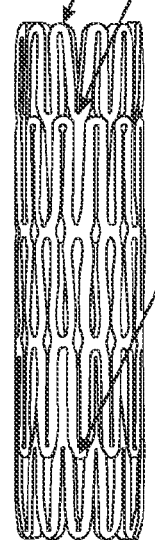

FIG. 15 is a schematic illustration of a frame for an implantable medical device in accordance with a seventh embodiment of the present invention. The frame may be for an implantable heart valve device for example. FIG. 16(a) shows the frame in a radially expanded state and FIG. 16(b) shows the frame in a radially contracted state.

The frame comprises a first end A and a second end B. In an embodiment, the frame is a cylindrical shape.

The frame is a multi-layered frame. The frame comprises a first member 201, which corresponds to a first layer, comprising a plurality of struts defining a plurality of cells and a second member 202, which corresponds to a second layer, comprising a plurality of struts. In this embodiment, the second member 202 does not define any cells.

The first member 201 is annular and defines a longitudinal direction which is parallel to the axis of the first member, a radial direction, and a circumferential direction. The first member 201 and the second member 202 are coupled at circumferentially distributed locations.

The first member 201 comprises a first end portion 201a and a second end portion 201b. The first end portion 201a is closer to the first end of the frame A and the second end portion 201b is closer to the second end of the frame B. The second member 202 comprises a first end portion 202a and a second end portion 202b.

The second member 202 overlaps the first end portion 201a of the first member 201 and extends beyond the first end portion 201a of the first member 201 in the longitudinal direction. The second member 202 overlaps the first end portion 201a of the first member 201 in the radial direction.

The first end portion 202a of the second member 202 is separate from the first end portion 201a of the first member 201.

The first member 201 and second member 202 according to the seventh embodiment are the same as for the first embodiment except for the configuration of the first struts 205. Furthermore, the struts in this frame are straight rod-like shapes, which connect at simple X or V shaped vertices. However, the struts may alternatively be configured as for the first embodiment for example. Repetition of describing the features which are the same as the first embodiment will be omitted.

Unlike in the first embodiment, in which the third struts 217, third vertices 210 and first struts 205 were all at the same radial distance from the axis, in this embodiment, the first struts 205 are coupled to the third vertices 210 by a coupling portion, which extends in a direction having a component in the radial direction. Thus the first struts 205 are radially spaced from the first member 201 along their entire length. The first struts 205 may extend in the longitudinal direction. The coupling portion 240 couples the first member 201 and the second member 202. In this case, the coupling portion 240 extends inwardly, but it may extend outwardly where the second member 202 is arranged outside the first member 201. The coupling portion 240 is connected at one end to the third vertex 210 and at the other end to the second end portion 205b of the first strut 205. The coupling portion may be integral with the second member 202 and/or the first member 201. Alternatively, the third struts 217, third vertices 210 and first struts 205 may be coupled as in the first embodiment for example.

The frame further comprises a third member 203. The third member 203 comprises a plurality of struts, and is coupled to the first member at circumferentially distributed locations, wherein the third member overlaps a second end portion of the first member and extends beyond the second end portion of the first member.

The third member 203 comprises a plurality of sixth struts 231 having a first end portion 231a and a second end portion 231b. The first end portion 231a is closer to the first end of the frame A. The sixth struts 231 are coupled to the first member 201 at the sixth vertices 220, i.e. at the first end 201a of the first member 201. In an embodiment, the sixth struts 231 are coupled to the sixth vertices 220 by a coupling portion 240, which extends in a direction having a component in the radial direction. Thus the sixth struts 231 are radially spaced from the first member 201 along their entire length. In an embodiment, the sixth struts 231 are spaced inside the first member 201. In an embodiment, the first struts 205 and the sixth struts 231 are radially spaced the same distance from the first member 201. The sixth struts 231 and the first struts 205 are interleaved. The sixth struts 231 may extend in the longitudinal direction. The coupling portion may be integral with the third member 203 and/or the first member 201. The third member 203 and the first member 201 may be integral.

The third member 203 is similar to the third member 203 of the first embodiment, thus repetition of describing the features which are the same as the first embodiment will be omitted. However the third member 203 in the seventh embodiment is coupled to the first member 201 at the first end 201a of the first member 201, instead of the second end 201b of the first member 201. Furthermore, the sixth struts 231 are coupled to the first member 201 at the sixth vertices 220. Thus the third member is circumferentially rotated compared with the second member 202, so that the first struts 205 and sixth struts 231 are not aligned, but are interleaved with each other. The third member 203 comprises the sixth struts 231 and the seventh struts 233, which form a trough shape, i.e. do not define a complete cell.

The device thus comprises three members: a first "outer" member 201; a third "upper inner" member 203 and a second "lower inner" member 202. As for the device according to the first embodiment, the absolute change in height of each of the second member 202 and the third member 203 is independent of the change in height of the first member 201. However, since the longitudinal struts of each of the second member 202 and third member 203 are coupled to the first member 201 at different vertices of the first member 201, the second member 202 and third member 203 move relative to each other between the crimped and expanded configurations, i.e. they are displaced. Specifically, during crimping, the first ends of the first struts 205a and the first ends of the sixth struts 231a move towards each other, and the second ends of the first struts 205b and the second ends of the sixth struts 231b move towards each other.

The second member 202 is coupled to the first member 201 at vertices at a first longitudinal location, and the third member 203 is coupled to the first member 201 at different vertices at a second, different longitudinal location. In other words, the vertices at which the second member 202 is coupled are longitudinally spaced from the vertices at which the third member 203 is coupled. This results in the second member 202 and the third member 203 moving in opposite longitudinal directions as the first member 201 expands and contracts.

In an embodiment, the second member 202 and third member 203 are coupled to the first member 201 at opposite ends of the first member 201.

In an embodiment, the vertices of the first member 201 at which the second member 202 is coupled to the first member 201 are circumferentially spaced from the vertices of the first member 201 at which the third member 203 is coupled to the first member 201.

Furthermore, the second member 202, which extends beyond the first member 201 at the first end A is connected to the first member 201 at the second end 201b, whereas the third member 203, which extends beyond the first member 201 at the second end B is connected to the first member 201 at the first end 201a. Thus the second member 202 extends beyond the first member 201 at the first end A but is connected to the first member closer to the second end B than the third member 203, which extends beyond the first member 201 at the second end B. The second member 202 and the third member 203 move in opposite directions to each other when the device expands or contracts, since they are coupled to the first member 201 at locations on the first member 201 which move relative to each other in the longitudinal direction. For example, one or both of the second member 202 and third member 203 may be coupled to the first member 201 at vertices or struts having a component in the circumferential direction, which are longitudinally spaced from the point at which the other of the second member 202 or third member 203 is coupled. The displacement of the second member 202 and the third member 203 between the expanded and contracted configurations counteracts the change of length produced by the second member 202 and the third member 203.

The expanded and crimped configurations can be seen in FIGS. 16(a) and (b). Point A corresponds to a sixth vertex 220, i.e. a vertex at which one of the longitudinal sixth struts 231 of the third member 203 connects to the lower ring of the first member 201. During crimping, point A moves towards the first end of the first struts 205a. In so doing, it pulls vertex B on the third member 203, i.e. it moves the sixth struts 231. Similarly, the third vertices 210 move towards the second end 231b of the sixth struts 231, and pull the first struts 205.

In an embodiment, zero change of total frame length between the expanded state and the contracted state can be achieved, as shown in FIG. 15. Effectively, the amount by which the sixth vertices 220 on the lower ring of the first member 201 move in the longitudinal direction relative to a fixed reference frame cancels out, or balances the amount by which the eighth vertices 232 on the upper ring of the third member 203, joined to the seventh vertices 230 by angled seventh struts 233, move in the longitudinal direction, relative to the seventh vertices 230. Equally, the amount by which the third vertices 210 on the upper ring of the first member 201 move in the longitudinal direction relative to a fixed reference frame cancels out, or balances the longitudinal displacement of the second vertices 211 of the second member 202 relative to the first vertices 209. During expansion the second 202 and third 203 members move in opposite directions to those during crimping. By controlling the angles and lengths of the angled struts of both the outer and inner members, it's possible to control the change of length between the expanded and contracted states.

The multiple layers allow the frame to have a reduced amount of length change or no length change between the radially contracted state and the radially expanded state, whilst maintaining radial stiffness. It is possible for the total frame length to change during crimping and expansion, but be the same in the initial and final states.

In an embodiment, the displacement of the second member 202 towards the second end B is more than the change in length of the second member 202. In an embodiment, the displacement of the third member 203 towards the first end A is more than the change in length of the third member 203. In an embodiment, the length of the frame in the radially contracted state is less than the length of the frame in the radially expanded state.

As the frame moves from the radially contracted state to the radially expanded state, the orientation of all of the struts other than the longitudinal struts, i.e. the first struts 205 and the sixth struts 231 changes. Thus when the frame moves from the radially expanded configuration to the radially contracted configuration, the longitudinal first struts 205 and sixth struts 231 do not change orientation, they simply move closer together in the circumferential direction, and relative to each other in the longitudinal direction as explained previously.

Any change in length of the frame is equal to the longitudinal displacement of the eighth vertices 232 from the sixth strut 231 minus the longitudinal displacement of the sixth vertices 220 relative to a fixed reference frame, combined with the longitudinal displacement of the second vertices 211 from the first struts 205 minus the longitudinal displacement of the third vertices 210 relative to a fixed reference frame. If both of these are zero, there is zero change in length of the frame.

In an embodiment, the changes of length of the first member 201 and the second member 202 are independent, and the changes of length of the first member 201 and the third member 203 are independent, the longitudinal displacement of the second member 202 depends on the change of length of the first member 201 and the longitudinal displacement of the third member 203 depends on the change of length of the first member 201. Thus the change of length of the second member 202 can be balanced by the displacement of the second member 202, and the change of length of the third member can be balanced by the displacement of the third member 203.

In the frame illustrated in FIG. 15 and FIGS. 16(a) and (b), the angles between the struts and lengths of the struts are equal within the first member 201. Furthermore, the second member 202 and third member 203 have the same strut configuration (i.e. the lengths of the struts and angles between the struts are the same). The inset box in FIG. 15 shows example dimensions and angles for the struts of the first member 201 and the third member 203 (and, since the second member 202 has the same configuration as the third member 203, the second member 202). As shown, in the second member 202 and the third member 203, the circumferential struts have a length of 3.57 mm, and are angled at 24.24 degrees from the circumferential direction. In the first member, each strut has a length of 4.22 mm, and is angled at 40.28 degrees. The first member defines 24 cells, arranged in two rings of 12 cells. The frame is 26 mm in diameter.

Figure 16C:
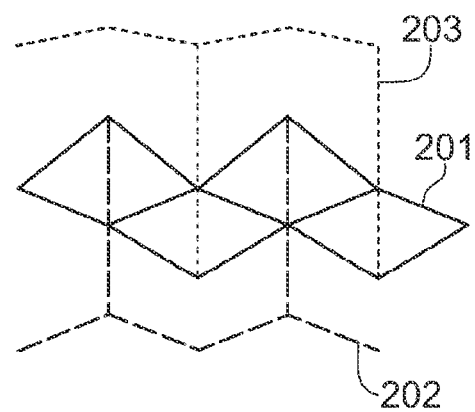
FIG. 16(c) shows a schematic illustration of an alternative frame configuration.

However, the struts may have different configurations. For example, FIG. 16(c) is a schematic illustration of a frame in which there are unequal strut lengths and angles within the first member 201 and different strut lengths and angles between the second and third members 202 and 203.

The frame may be formed by any of the methods described herein.

While certain embodiments have been described, these embodiments have been presented by way of example only, and are not intended to limit the scope of the inventions. Indeed the novel methods and apparatus described herein may be embodied in a variety of other forms; furthermore, various omissions, substitutions and changes in the form of methods and apparatus described herein may be made without departing from the spirit of the inventions. The accompanying claims and their equivalents are intended to cover such forms of modifications as would fall within the scope and spirit of the inventions.

The invention claimed is:

1. An implantable heart valve device comprising:
   a frame comprising:
   a first member, comprising a plurality of struts defining a plurality of cells, wherein the first member is annular and defines a longitudinal direction which is parallel to an axis of the first member, a radial direction, and a circumferential direction;
   a second member, comprising a plurality of struts and coupled to the first member at multiple circumferentially distributed locations, wherein the second member overlaps a first end portion of the first member and extends beyond the first end portion of the first member;
   a skirt coupled to the frame;
   a plurality of leaflets coupled to the frame through the skirt; and
   a third member, the third member comprising a plurality of struts and being coupled to the first member at multiple circumferentially distributed locations, wherein the third member overlaps a second end portion of the first member and extends beyond the second end portion of the first member.

2. The implantable heart valve device according to claim 1, wherein a first end portion of the second member is separate from the first end portion of the first member.

3. The implantable heart valve device according to claim 1, wherein the first member is integral.

4. The implantable heart valve device according to claim 1, wherein the second member is annular and is radially displaced from the first member such that one of the first member and the second member is arranged around the other.

5. The implantable heart valve device according to claim 1, wherein the frame is configured to be radially contracted and expanded, between a radially contracted state and a radially expanded state, wherein a change in length of the first member between the radially contracted state and the radially expanded state is independent of a change in length of the second member between the radially contracted state and the radially expanded state.

6. The implantable heart valve device according to claim 1, wherein the second member comprises a plurality of first struts having a first end and a second end, and wherein the direction from the first end to the second end has a component in the longitudinal direction and is orthogonal to the circumferential direction.

7. The implantable heart valve device according to claim 1, wherein a radial distance between the first member and the second member at the first end portion of the first member is greater than 40 microns.

8. The implantable heart valve device according to claim 1, wherein the first member defines more rings of cells than the second member.

9. The implantable heart valve device according to claim 1, wherein the plurality of struts of the second member defines a plurality of cells.

10. The implantable heart valve device according to claim 1, wherein the frame is formed by additive manufacturing.

11. A method of manufacturing an implantable heart valve device comprising the steps of:
   providing a frame by forming a plurality of struts defining a plurality cells by additive manufacturing,
   forming a first member of the frame, the first member comprising a plurality of struts defining a plurality of cells, wherein the first member is annular and defines a longitudinal direction that is parallel to an axis of the first member, a radial direction, and a circumferential direction;
   forming a second member of the frame, the second member comprising a plurality of struts, coupled to the first member at multiple circumferentially distributed locations, wherein the second member overlaps a first end portion of the first member and extends beyond the first end portion of the first member, wherein a first end portion of the second member is separate from the first end portion of the first member, and wherein the first member and the second member are integrally formed;
   coupling a skirt to the frame; and
   coupling a plurality of leaflets to the frame through the skirt.

12. The method of claim 11, further comprising:
   forming a plurality of support structures;
   wherein forming the struts comprises:
   forming a ring comprising a plurality of struts on multiple support structures, wherein the struts extend away from the support structures; and
   wherein the method further comprises removing the support structures from the struts.

13. The method of claim 11, further comprising:
   forming a plurality of support structures;
   wherein forming the first member comprises forming a first ring comprising a plurality of struts on multiple support structures, wherein the struts extend away from the support structures,
   wherein the method further comprises removing the support structures from the struts.

14. The method of claim 13, further comprising:
   forming a plurality of further support structures coupling the first member and the second member at the first end portion of the first member.

15. The method of any of claim 11, wherein a radial distance between the first member and the second member at the first end portion of the first member is greater than 40 microns.

* * * * *